(12) United States Patent
Kaplan et al.

(10) Patent No.: US 8,129,141 B2
(45) Date of Patent: Mar. 6, 2012

(54) FIBROUS PROTEIN FUSIONS AND USE THEREOF IN THE FORMATION OF ADVANCED ORGANIC/INORGANIC COMPOSITE MATERIALS

(75) Inventors: David L. Kaplan, Concord, MA (US); Jia Huang, Medford, MA (US); Cheryl Wong Po Foo, Palo Alto, CA (US); Rajesh Naik, Dayton, OH (US); Anne George, Chicago, IL (US)

(73) Assignees: Trustees of Tufts College; The United States of America as represented by the Secretary of the Air Force AFMCLO/JAZ, Washington, DC (US); The Board of Trustees of the University of Illinois

( * ) Notice: Subject to any disclaimer, the term of this patent is extended or adjusted under 35 U.S.C. 154(b) by 0 days.

(21) Appl. No.: 13/097,538

(22) Filed: Apr. 29, 2011

(65) Prior Publication Data

US 2011/0275788 A1    Nov. 10, 2011

Related U.S. Application Data

(63) Continuation of application No. 11/794,934, filed as application No. PCT/US2006/001536 on Jan. 17, 2006, now Pat. No. 7,960,509.

(60) Provisional application No. 60/644,264, filed on Jan. 14, 2005.

(51) Int. Cl.
*C12P 1/00* (2006.01)
(52) U.S. Cl. ......................................... 435/41
(58) Field of Classification Search ................... None
See application file for complete search history.

(56) References Cited

U.S. PATENT DOCUMENTS 6,291,428 B1    9/2001 Macaulay et al.
2004/0005363 A1  1/2004 Tsukada et al.

FOREIGN PATENT DOCUMENTS

| EP | 0 985 732 A2 | 3/2000 |
|---|---|---|
| EP | 1 413 585 A2 | 4/2004 |
| WO | WO 02/00016 A1 | 1/2002 |

OTHER PUBLICATIONS

Meinel, et al., "Engineering bone-like tissue in vitro using human bone marrow stem cells and silk scaffolds" *Wiley Periodicals, Inc.*, pp. 25-34, 2004.
Sofia, et al., "Functionalized silk-based biomaterials for bone formation," *Journal of Biomedical Materials Research*, vol. 54, pp. 139-148, 2001.
Kong, et al., "Silk fibroin regulated mineralization of hydroxyapatite nanocrystals", *Journal of Crystal Growth* vol. 270, pp. 197-202, 2004.
Hunter, et al., "Induction of collagen mineralization by a bone sialoprotein-decorin chemeric protein," pp. 496-502, 2001.
Wong Po Foo, et al., "Novel nanocomposites from spider silk-silica fusion (chimeric) proteins," *PNAS* vol. 103 No. 25, pp. 9428-9433, Jun. 20, 2006.
Demura, Makoto, et al., "Immobilization of Biocatalysts with Bombyx mori Silk Fibroin by Several Kinds of Physical Treatment and its Application to Glucose Sensors," Biosensors. pp. 361-372 (1989).
Branden et al., "Introduction to Protein Structure Second Edition," Garland Publishing Inc., New York, 1999.
Witkowski et al., Biochemistry, 38, 11643-11650, 1999.
Wishart et al., Journal of Biological Chemistry, vol. 270, No. 45, pp. 26782-26785, 1995.
Kisselev, Structure, vol. 10, pp. 8-9, 2002.

*Primary Examiner* — Suzanne M Noakes
*Assistant Examiner* — Jae W Lee
(74) *Attorney, Agent, or Firm* — Nixon Peabody LLP

(57) ABSTRACT

The claimed invention provides a fusion polypeptide comprising a fibrous protein domain and a mineralization domain. The fusion is used to form an organic-inorganic composite. These organic-inorganic composites can be constructed from the nano- to the macro-scale depending on the size of the fibrous protein fusion domain used. In one embodiment, the composites can also be loaded with other compounds (e.g., dyes, drugs, enzymes) depending on the goal for the materials, to further enhance function. This can be achieved during assembly of the material or during the mineralization step in materials formation.

10 Claims, 15 Drawing Sheets

Fusion proteins of spider silk and dentin matrix protein 1 (DMP1)

1. Spider silk (CRGD-15mer) - full length DMP1 (Mw = 92.9 kDa)

CRGD-15mer (506 aa)       full length DMP1 (474 aa)

2. Spider silk (CRGD-15mer) -C-terminal DMP1 (Mw = 58.9 kDa)

CRGD-15mer (506 aa)       C-terminal DMP1 (156 aa)

3. Spider silk (CRGD-15mer) – (CD1 + pA + pB + CD2)

CRGD-15mer (506 aa)     (37aa)

FIG. 1A

Fusion protein of spider silk and bone sialoprotein domain (BSP)

1. Spider silk (15mer)- sialoprotein domain (Mw = 42.7 kDa)

15mer (495 aa)       BSP (48 aa)

2. Spider silk (CRGD-15mer) – sialoprotein domain (Mw = 48.1 kDa)

CRGD-15mer (499 aa)       BSP (48 aa)

FIG. 1B

CRGD-15mer-CDMP1: (SEQ ID NO: 9): a fusion protein
of (SEQ ID NO: 5) (dark grey highlight) and (SEQ ID
NO: 6) (light grey highlight)

MASMTGGQQMGRCRGDTSGRGGLGGQGAGAAAAAGGAGQGGYGGLGSQGTS
GRGGLGGQGAGAAAAAGGAGQGGYGGLGSQGTSGRGGLGGQGAGAAAAGG
AGQGGYGGLGSQGTSGRGGLGGQGAGAAAAAGGAGQGGYGGLGSQGTSGRG
GLGGQGAGAAAAAGGAGQGGYGGLGSQGTSGRGGLGGQGAGAAAAAGGAGQ
GGYGGLGSQGTSGRGGLGGQGAGAAAAAGGAGQGGYGGLGSQGTSGRGGLG
GQGAGAAAAAGGAGQGGYGGLGSQGTSGRGGLGGQGAGAAAAAGGAGQGGY
GGLGSQGTSGRGGLGGQGAGAAAAAGGAGQGGYGGLGSQGTSGRGGLGGQG
AGAAAAAGGAGQGGYGGLGSQGTSGRGGLGGQGAGAAAAAGGAGQGGYGGL
GSQGTSGRGGLGGQGAGAAAAAGGAGQGGYGGLGSQGTSGRGGLGGQGAGA
AAAAGGAGQGGYGGLGSQGTSGRGGLGGQGAGAAAAAGGAGQGGYGGLGSQ
GTSRGDCGSRGDNPDNTSQTGDQRDSESSEEDRLNTFSSSESQSTEEQGDS
ESNESLSLSEESQESAQDEDSSSQEGLQSQSASRESRSQESQSEEDSRSEE
NRDSDSQDSSRSKEESNSTGSTSSSEEDNHPKNIEADNRKLIVDAYHNKPI
GDQDDNDCQDGY         (SEQ ID NO: 9)

*FIG. 2*

CRGD-15mer-DMP1 (SEQ ID NO: 10): a fusion protein of (SEQ ID NO: 5) (dark grey highlight) and (SEQ ID NO: 7) (light grey highlight)

MASMTGGQQMGRCRGDTSGRGGLGGQGAGAAAAAGGAGQGGYGGLGSQGTS
GRGGLGGQGAGAAAAAGGAGQGGYGGLGSQGTSGRGGLGGQGAGAAAAAGG
AGQGGYGGLGSQGTSGRGGLGGQGAGAAAAAGGAGQGGYGGLGSQGTSGRG
GLGGQGAGAAAAAGGAGQGGYGGLGSQGTSGRGGLGGQGAGAAAAAGGAGQ
GGYGGLGSQGTSGRGGLGGQGAGAAAAAGGAGQGGYGGLGSQGTSGRGGLG
GQGAGAAAAAGGAGQGGYGGLGSQGTSGRGGLGGQGAGAAAAAGGAGQGGY
GGLGSQGTSGRGGLGGQGAGAAAAAGGAGQGGYGGLGSQGTSGRGGLGGQG
AGAAAAAGGAGQGGYGGLGSQGTSGRGGLGGQGAGAAAAAGGAGQGGYGGL
GSQGTSGRGGLGGQGAGAAAAAGGAGQGGYGGLGSQGTSGRGGLGGQGAGA
AAAAGGAGQGGYGGLGSQGTSGRGGLGGQGAGAAAAAGGAGQGGYGGLGSQ
GTSRGDCGSLPVARYQNTESESSEERTGNLAQSPPPPMANSDHTDSSESGE
ELGSDRSQYRPAGGLSKSAGMDADKEEDEDDSGDDTFGDEDNGPGPEERQW
GGPSRLDSDEDSADTTQSSEDSTSQENSAQDTPSDSKDHHSDEADSRPEAG
DSTQDSESEEYRVGGGSEGESSHGDGSEFDDEGMQSDDPGSTRSDRGHTRM
SSADISSEESKGDHEPTSTQDSDDSQDVEFSSRKSFRRSRVSEEDDRGELA
DSNSRETQSVSTEDFRSKEESRSETQEDTAETQSQEDSPEGQDPSSESSEE
AGEPSQESSSESQEGVASESRGDNPDNTSQTGDQRDSESSEEDRLNTFSSS
ESQSTEEQGDSESNESLSLSEESQESAQDEDSSSQEGLQSQSASRESRSQE
SQSEEDSRSEENRDSDSQDSSRSKEESNSTGSTSSSEEDNHPKNIEADNRK
LIVDAYHNKPIGDQDDNDCQDGY        (SEQ ID NO: 10)

*FIG. 3*

15mer-BSP   (SEQ ID NO: 11): a fusion protein of (SEQ
ID NO: 4) (light grey highlight) and (SEQ ID NO: 8)
 (dark grey highlight)

MASMTGGQQMGRGSAMASGRGGLGGQGAGAAAAAGGAGQGGYGGLGSQGTS
GRGGLGGQGAGAAAAAGGAGQGGYGGLGSQGTSGRGGLGGQGAGAAAAAGG
AGQGGYGGLGSQGTSGRGGLGGQGAGAAAAAGGAGQGGYGGLGSQGTSGRG
GLGGQGAGAAAAAGGAGQGGYGGLGSQGTSGRGGLGGQGAGAAAAAGGAGQ
GGYGGLGSQGTSGRGGLGGQGAGAAAAAGGAGQGGYGGLGSQGTSGRGGLG
GQGAGAAAAAGGAGQGGYGGLGSQGTSGRGGLGGQGAGAAAAAGGAGQGGY
GGLGSQGTSGRGGLGGQGAGAAAAAGGAGQGGYGGLGSQGTSGRGGLGGQG
AGAAAAAGGAGQGGYGGLGSQGTSGRGGLGGQGAGAAAAAGGAGQGGYGGL
GSQGTSGRGGLGGQGAGAAAAAGGAGQGGYGGLGSQGTSGRGGLGGQGAGA
AAAAGGAGQGGYGGLGSQGTSGRGGLGGQGAGAAAAAGGAGQGGYGGLGSQ
GTSEFPVQSSSDSSEENGNGDSSEEEEEEEENSNEEENNEENEDSDGNEDK
LHHHHHH     (SEQ ID NO: 11)

FIG. 4

CRGD-15mer-BSP (SEQ ID NO: 12): a fusion protein of
(SEQ ID NO: 5) (light grey highlight) and (SEQ ID
NO: 8) with linker MASMTGGQQMGRGSCRGDTSGRGGLGGQGAGAAAAAGGAGQGGYGGLGSQG
TSGRGGLGGQGAGAAAAAGGAGQGGYGGLGSQGTSGRGGLGGQGAGAAAA
GGAGQGGYGGLGSQGTSGRGGLGGQGAGAAAAAGGAGQGGYGGLGSQGTSG
RGGLGGQGAGAAAAAGGAGQGGYGGLGSQGTSGRGGLGGQGAGAAAAAGGA
GQGGYGGLGSQGTSGRGGLGGQGAGAAAAAGGAGQGGYGGLGSQGTSGRGG
LGGQGAGAAAAAGGAGQGGYGGLGSQGTSGRGGLGGQGAGAAAAAGGAGQG
GYGGLGSQGTSGRGGLGGQGAGAAAAAGGAGQGGYGGLGSQGTSGRGGLGG
QGAGAAAAAGGAGQGGYGGLGSQGTSGRGGLGGQGAGAAAAAGGAGQGGYG
GLGSQGTSGRGGLGGQGAGAAAAAGGAGQGGYGGLGSQGTSGRGGLGGQGA
GAAAAAGGAGQGGYGGLGSQGTSGRGGLGGQGAGAAAAAGGAGQGGYGGLG
SQGTSRGDCGSE**NPVQSSSDSSEENGNGDSSEEEEEEEENSNEEDNNE
NEDSDGNEID**KLHHHHHH    (SEQ ID NO: 12)

*FIG. 5*

ROUND 1

ROUND 3

CRGD15mer-R5

```
MASMTGGQQM GRGSCRGDTS GRGGLGGQGA GAAAAAGGAG QGGYGGLGSQ GTSGRGGLGG    60
QGAGAAAAAG GAGQGGYGGL GSQGTSGRGG LGGQGAGAAA AAGGAGQGGY GGLGSQGTSG   120
RGGLGGQGAG AAAAAGGAGQ GGYGGLGSQG TSGRGGLGGQ GAGAAAAAGG AGQGGYGGLG   180
SQGTSGRGGL GGQGAGAAAA AGGAGQGGYG GLGSQGTSGR GGLGGQGAGA AAAAGGAGQG   240
GYGGLGSQGT SGRGGLGGQG AGAAAAAGGA GQGGYGGLGS QGTSGRGGLG GQGAGAAAAA   300
GGAGQGGYGG LGSQGTSGRG GLGGQGAGAA AAAGGAGQGG YGGLGSQGTS GRGGLGGQGA   360
GAAAAAGGAG QGGYGGLGSQ GTSGRGGLGG QGAGAAAAAG GAGQGGYGGL GSQGTSGRGG   420
LGGQGAGAAA AAGGAGQGGY GGLGSQGTSG RGGLGGQGAG AAAAAGGAGQ GGYGGLGSQG   480
TSGRGGLGGQ GAGAAAAAGG AGQGGYGGLG SQGTSRGDCG SEFSSKKSGS YSGSKGSKRR   540
ILCGRHHHHH H                                                       551
      (SEQ ID NO: 24)
```

FIG. 7A

15mer-R5

```
MHHHHHHSSG LVPRGSGMKE TAAAKFERQH MDSPDLGTDD DDKAMASGRG GLGGQGAGAA    60
AAAGGAGQGG YGGLGSQGTS GRGGLGGQGA GAAAAAGGAG QGGYGGLGSQ GTSGRGGLGG   120
QGAGAAAAAG GAGQGGYGGL GSQGTSGRGG LGGQGAGAAA AAGGAGQGGY GGLGSQGTSG   180
RGGLGGQGAG AAAAAGGAGQ GGYGGLGSQG TSGRGGLGGQ GAGAAAAAGG AGQGGYGGLG   240
SQGTSGRGGL GGQGAGAAAA AGGAGQGGYG GLGSQGTSGR GGLGGQGAGA AAAAGGAGQG   300
GYGGLGSQGT SGRGGLGGQG AGAAAAAGGA GQGGYGGLGS QGTSGRGGLG GQGAGAAAAA   360
GGAGQGGYGG LGSQGTSGRG GLGGQGAGAA AAAGGAGQGG YGGLGSQGTS GRGGLGGQGA   420
GAAAAAGGAG QGGYGGLGSQ GTSGRGGLGG QGAGAAAAAG GAGQGGYGGL GSQGTSGRGG   480
LGGQGAGAAA AAGGAGQGGY GGLGSQGTSG RGGLGGQGAG AAAAAGGAGQ GGYGGLGSQG   540
TSSSKKSGSY SGSKGSKRRI L                                            561
      (SEQ ID NO: 25)
```

FIG. 7B

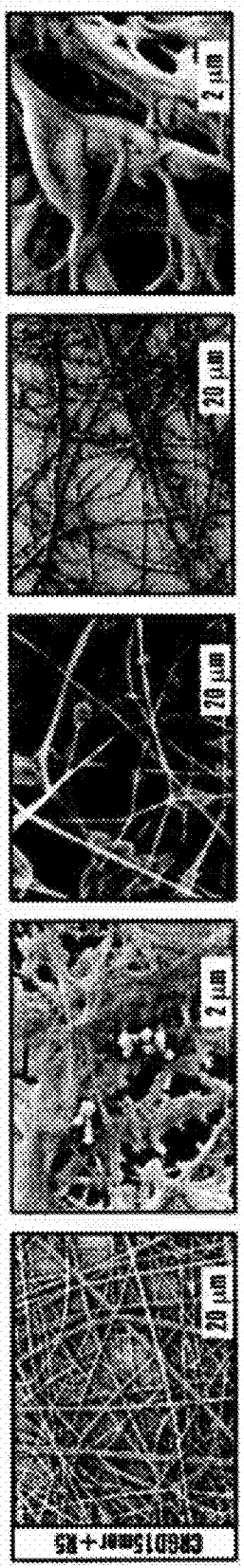

FTIR ANALYSIS OF RECOMBINANT PROTEIN CONSISTING OF SPIDER SILK SEQUENCE AND DENTIN MATRIX PROTEIN C-TERMINAL SEQUENCE.

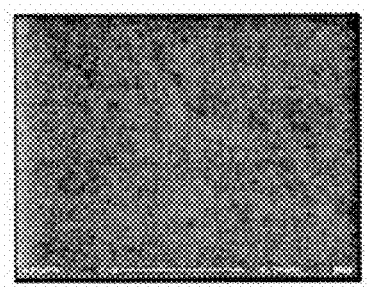
*FIG. 13A1*
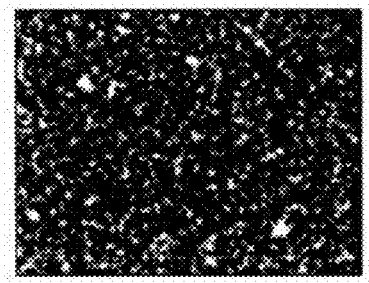
*FIG. 13A2*
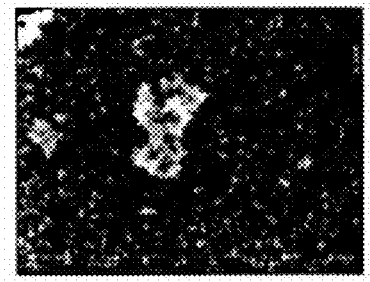
*FIG. 13A3*
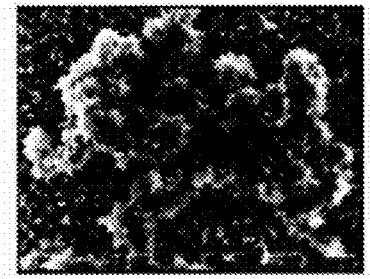
*FIG. 13A4*
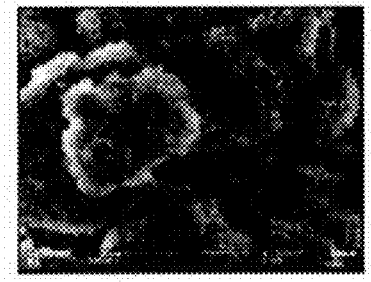
*FIG. 13A5*
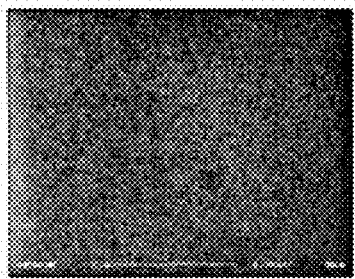
*FIG. 13B1*
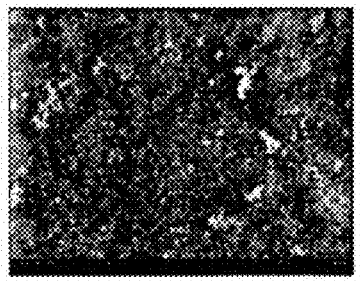
*FIG. 13B2*
*FIG. 13B3*
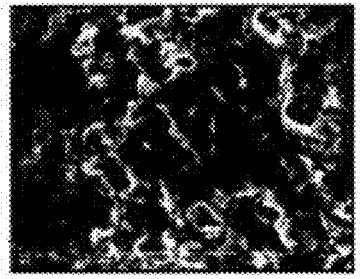
*FIG. 13B4*
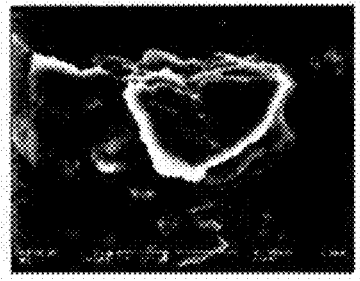
*FIG. 13B5*

FIBROUS PROTEIN FUSIONS AND USE THEREOF IN THE FORMATION OF ADVANCED ORGANIC/INORGANIC COMPOSITE MATERIALS

CROSS-REFERENCED TO RELATED APPLICATIONS

This application is a continuation of U.S. Ser. No. 11/794,934 filed on Jan. 14, 2008, which is a 371 National Phase Entry Application of International Application No. PCT/US2006/01536, filed Jan. 17, 2006, which designates the U.S., and which claims the benefit under 35 U.S.C. §119(e) of U.S. Provisional Patent Application No. 60/644,264, filed Jan. 14, 2005, the contents of which are incorporated herein by reference in their entireties.

GOVERNMENT SUPPORT

This invention was made with Government Support under FA9550041-0363 awarded by the U.S. Air Force and EB003210-01 and DE011657 awarded by the National Institutes of Health. The government has certain rights in the invention.

BACKGROUND OF THE INVENTION

Many biomedical procedures require the provision of healthy tissue to counteract the disease process or trauma being treated. This work is often hampered by the tremendous shortage of tissues available for transplantation and/or grafting. Tissue engineering may ultimately provide alternatives to whole organ or tissue transplantation.
In order to generate engineered tissues, various combinations of biomaterials and living cells are currently being investigated. Although attention is often focused on the cellular aspects of the engineering process, the design characteristics of the biomaterials also constitute a major challenge in this field.

In recent years, the ability to regenerate tissues and to control the properties of the regenerated tissue have been investigated by trying to specifically tune the mechanical or chemical properties of the biomaterial scaffold (Kim et al., 1997; Kohn et al. 1997). The majority of work has involved the incorporation of chemical factors into the material during processing, or the tuning of mechanical properties by altering the constituents of the material.

The foregoing methods have been used in an attempt to utilize chemical or mechanical signaling to affect changes in the proliferation and/or differentiation of cells during tissue regeneration. Despite such efforts there remains in the art a need for improved biomaterials, including composite materials, particularly those with a better capacity to support complex tissue growth in vitro (in cell culture) and in vivo (upon implantation).

SUMMARY OF THE INVENTION

The claimed invention provides a fusion polypeptide comprising a fibrous protein domain and a mineralization domain.
In one embodiment the fibrous protein domain is obtained from silk, collagens, coiled-coiled leucine zipper proteins, elastins, keratins, actins, and tubulins.
For example, in one preferred embodiment, the fibrous protein domain comprises an amino acid sequence from the silk protein Spidroin 1, such as the fibrous protein domains indicated by (SEQ ID NO: 1) or (SEQ ID NO: 3), which are derived from Spiroidin 1 of *Nephila clavipes*. A recombinant fibrous protein domain can be generated, which has multiple repeats of a fibrous protein domain.

In one embodiment, the fibrous domain sequence of (SEQ ID NO: 1) is repeated 15 times throughout the fibrous protein domain, which is used in the fusion proteins of the invention, i.e., the fibrous protein domain sequence indicated by (SEQ ID NO: 4), referred to herein as 15mer.

In one embodiment, a fibrous domain sequence of (SEQ ID NO: 1) is repeated 15 times throughout the fibrous protein domain that is used in the fusion proteins of the invention and has a CRGD (SEQ ID NO: 2) linker sequence, i.e. the fibrous protein domain sequence indicated by (SEQ ID NO: 5), referred to herein as CRGD-15mer.

In one embodiment, the fusion polypeptide of the invention has a mineralizing domain that is capable of inducing the formation of hydroxyapatite, silica, cadmium sulfide or magnetite.

In one embodiment, the mineralization domain is obtained from dentin matrix protein 1 (DMP1), bone sialoprotein (BSP), or silaffin-1 (Sil1) protein.

In one embodiment, the mineralization domain is derived from dentin matrix protein 1 (DMP1) and is (SEQ ID NO: 6) or (SEQ ID NO: 7).

In one embodiment, the mineralization domain is derived from bone sialoprotein (BSP) and is (SEQ ID NO: 8).

In one embodiment, the mineralizing domain is selected from the group consisting of the 19 amino-acid R5 peptide of the Sil1 protein (SEQ ID NO: 17), the R2 peptide of the Sil1 protein (SEQ ID NO: 18), the 19 amino-acid R3 peptide of the Sil1 protein (SEQ ID NO: 19), the 19 amino-acid R6 peptide of the Sil1 protein (SEQ ID NO: 20) and the 15 amino-acid R1 peptide of the Sil1 protein (SEQ ID NO: 21).

The invention also provides for the following fusion polypeptides that comprise a fibrous protein domain and a mineralization domain: the fusion polypeptide (SEQ ID NO: 9), the fusion polypeptide (SEQ ID NO: 10), the fusion polypeptide (SEQ ID NO: 11), the fusion polypeptide (SEQ ID NO: 12), a fusion polypeptide comprising a fusion of the 15 mer silk fibrous protein domain (SEQ ID NO: 4) and the R5 peptide of the Sil1 protein (SEQ ID NO: 17) and a fusion polypeptide comprising a fusion of the CRGD-15 mer silk fibrous protein domain (SEQ ID NO: 5) and the R5 peptide of the Sil1 protein (SEQ ID NO: 17).

A method for forming a fibrous protein inorganic-composite material is also provided. The method comprises (a) contacting the fusion proteins of the invention with an inorganic material capable of mineralizing for a sufficient period of time to allow mineralization of the inorganic material.

In one preferred embodiment, the fusion proteins of the invention are formed into a silk film, foam or sponge prior to deposition of inorganic material (mineralization).

In one embodiment, the inorganic material is capable of forming hydroxyapatite or silica.

In one embodiment, the fiber, film, or sponge further comprises an agent.

In one embodiment, the inorganic coating formed on the fibrous protein comprises an agent.

In one embodiment, the agent is selected from the group consisting of a protein, peptide, nucleic acid, PNA, aptamer, antibody or a small molecule.

The claimed invention also provides for biomaterial products produced by the methods of the invention.

BRIEF DESCRIPTION OF FIGURES

FIGS. 1A and 1B show diagrammatic illustrations of fibrous protein domain-mineralization domain fusion proteins. FIG. 1A shows three claimed fusion proteins composed of a spider silk fibrous protein domain ((CRGD-15mer) (See (SEQ ID NO: 5)) and a dentin matrix protein 1 (DMP1) mineralization domain. The fusion proteins contain a mineralization domain of either 1) the full length amino acid sequence of DMP1 (See (SEQ ID NO: 7)), 2) the C-terminal end of DMP1, (See (SEQ ID NO: 6)) or a composite sequence based on DMP1, which contains the collagen binding domain 1 (CD1) of DMP1, two acidic clusters in DMP1 that are responsible for hydroxyapatite nucleation (pA and pB) and the collagen binding domain 2 (CD2) of DMP1. FIG. 1B shows a diagram of two fusion proteins, 1) fusion of a spider silk fibrous protein domain (CRGD-15mer (See (SEQ ID NO: 5)) and a bone sialoprotein mineralizing domain (BSP) (See (SEQ ID NO: 8)) and 2) fusion of a spider silk fibrous protein domain 15-mer (without CRGD (SEQ ID NO: 2) linker) (See (SEQ ID NO: 4)) and a bone sialoprotein mineralizing domain (BSP) (See SEQ ID NO: 8).

FIG. 2 shows the sequence of the fusion protein CRGD-15mer-CDMP1 (SEQ ID NO: 9). CRGD-15mer-CDMP1 is a fusion protein of a spider silk fibrous protein domain ((CRGD-15mer) (See, SEQ ID NO: 5), which is indicated by a dark grey highlight, and the C-terminal end of DMP1 mineralizing domain (See, SEQ ID NO: 6), which is indicated with light grey highlight.

FIG. 3 shows the sequence of the fusion protein CRGD-15mer-DMP1 (SEQ ID NO: 10). CRGD-15mer-DMP1 is a fusion protein of spider silk fibrous protein domain ((CRGD-15mer) (See, SEQ ID NO: 5), which is indicated by a dark grey highlight, and the full length sequence of DMP1 mineralizing domain (See, SEQ ID NO: 7), which is indicated with light grey highlight.

FIG. 4 shows the sequence of the fusion protein 15mer-BSP (SEQ ID NO: 11). 15mer-BSP is a fusion protein of spider silk fibrous protein domain ((15mer) (See, SEQ ID NO: 4), which is indicated by light grey highlight, and a mineralizing domain of bone sialoprotein (BSP) (SEQ ID NO: 8), which is indicated with dark grey highlight.

FIG. 5 shows the sequence of the fusion protein CRGD-15mer-BSP (SEQ ID NO: 12). CRGD-15mer-BSP a fusion protein of spider silk fibrous protein domain ((CRGD-15mer) (See, SEQ ID NO: 5), which is indicated by light grey highlight, and a mineralizing domain of bone sialoprotein (BSP) (SEQ ID NO: 8), which is indicated with dark grey highlight. A linker sequence between the two domains is also present.

FIG. 6A, image of silk film morphology prior to mineralization (HFIP+MeOH). FIG. 6B, image of silk film morphology after one round of mineralization. FIG. 6C, image of silk film morphology after three rounds of mineralization.

FIGS. 7A to 7B show the sequence of the fusion proteins CRGD15mer-R5 (SEQ ID NO: 24) and 15mer-R5 (SEQ ID NO: 25) as described in Example II. The underlined sequence represents the monomeric repeat unit selected and used in the design of the recombinant proteins based on the consensus sequence of spidroin1 (Masp1) native sequence of *Nephila clavipes* (Accession #P19837).

FIGS. 9A to 9E show SEM images of untreated and methanol treated electropun CRGD15mer-R5 (SEQ ID NO: 24) silk fibers before, during and after silicification reactions, as described in Example 2. FIG. 9A, untreated electrospun CRGD15mer-R5 (SEQ ID NO: 24) silk fibers. FIG. 9B, electrospun CRGD15mer-R5 (SEQ ID NO: 24) silk fibers methanol treated before silification. FIGS. 9C, 9D and 9E, electrospun CRGD15mer-R5 (SEQ ID NO: 24) silk fibers during silification at 20 um and 2 um scale.

FIGS. 13(A1) to 13(A5) and 13(B1) to 13(B5) show Scanning Electron Microscopy (SEM) surface morphologies of recombinant spider silk films after soaking in 1.5×SBF for various periods of time, as described in Example 1. FIG. 13(A1)-FIG. 13(A5), SS15m-CDMP1 soaked in 1.5×SBF for 0, 3, 7, 14 and 21 days: FIG. 13(A1)-FIG. 13(A5) respectively. FIG. 13(B1)—FIG. 13(B5), SS15m soaked in 1.5× SBF for 0, 3, 7, 14 and 21 days: FIG. 13(B1)-FIG. 13(B5) respectively. Scale bars are 2 µm.

(FIG. 14A) image of flake-like apatite; (FIG. 14B) electron diffraction pattern; (FIG. 14C) high-resolution image of apatite crystal.

DESCRIPTION OF THE INVENTION

Figure 6A:
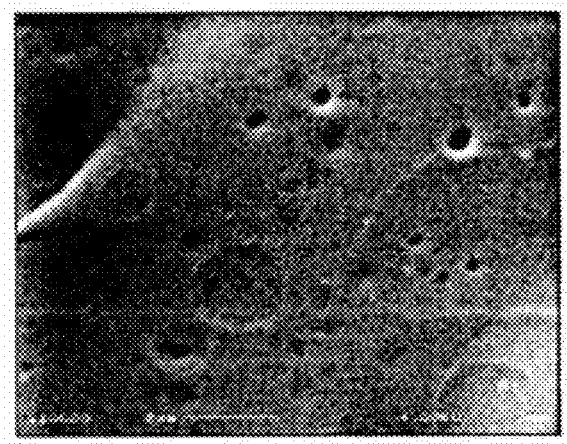
FIGS. 6A to 6C show scanning electron microscope (SEM) images of recombinant silk film made from CRGD-15mer-CDMP1 (SEQ ID NO: 9), See Example 1.

Fibrous proteins represent an important category of proteins in biology, forming native structural entities both internally in organisms (e.g., collagens) and externally (such as spun silk fibers for webs and cocoons). As an example, silk proteins from spiders and insects provide a number of valuable materials features. When combined with functional domains, then the materials properties available from silks become significantly expanded. In accordance with the present invention, various domains from biology known to promote the formation of inorganic structures, e.g., promote formation of minerals, have been combined with a fibrous protein domain. Thus, these new fusion (composite) materials offer the benefits of the fibrous protein material features (e.g, silks) plus the benefit of the inorganic mineralization domains (e.g., hardness).

In one embodiment, the present invention provides a fusion polypeptide comprising a fibrous protein domain and a mineralization domain. The fusion is used to form an organic-inorganic composite. These organic-inorganic composites can be constructed from the nano- to the macro-scale depending on the size of the fibrous protein fusion domain used. In one embodiment, the composites can also be loaded with other compounds (e.g., dyes, drugs, enzymes) depending on the goal for the materials, to further enhance function. This can be achieved during assembly of the material or during the mineralization step in materials formation.

The fusion polypeptides of the present invention can be used for production of silk biomaterials, e.g., fibers, films, foams and mats. See, WO 03/022909. An all-aqueous process may be used. See, WO 03/022909.

In another embodiment, the invention provides a method for forming a composite material. The method comprises contacting a template formed from a fusion polypeptide of the invention with a suitable inorganic material for a sufficient period of time to allow mineralization of the inorganic material thus forming an inorganic coating on the template.

In one embodiment the template is in the form of a fiber, film, or sponge.

In an additional embodiment, growth factors, biological components or others agents, including therapeutic agents, are incorporated into the inorganic coating. The growth factors, biological components or other agents, can be incorporated during the formation of the template or during the crystallization process. Such composites can be used to deliver such components to cells and tissues. The ability to incorporate growth factors, biological regulators, enzymes, therapeutics, or cells in the construct of the present invention provides for stabilization of these components for long term release and stability, as well as better control of activity and release.

The products produced by these methods offer new options in the formation of scaffolds for biomaterials, tissue engineering applications and drug delivery. While the templates are useful in and of themselves, the ability to form inorganic coatings with controlled thickness leads to control of mechanical properties (e.g., stiffness) and biological interactions, such as for bone formation. Furthermore, the ability to control these processes allows one to match structural and functional performance of scaffolds for specific tissue targets and needs.

In another embodiment, the underlying template (e.g., fusion polypeptide formed into a film etc.) can be removed or etched away to generate porous networks, tubes, or lamellar sheets of inorganic material. These materials are useful directly as biomaterial scaffolds, for control of cell and tissue growth (e.g., as nerve conduits, bone conduits) and for non-biological applications (e.g., filtration and separation media, catalysis, decontamination (directly or if filled with appropriate chemical or enzymes), radar chaff, coatings in general, and many related needs, for example, inorganic fillers to toughen materials that can also be filled with a second component.

The fusion polypeptides may be created, for example, by chemical synthesis, or by creating and translation a polynucleotide in which the peptide regions are encoded in the desired relationship.

It is to be understood that while the invention has been described in conjunction with the preferred specific embodiments thereof that the foregoing description as well as the examples that follow are intended to illustrate and not limit the scope of the invention. Other aspects, advantages and modifications within the scope of the invention will be apparent to those skilled in the art to which the invention pertains.

Fibrous Protein Domains

Silks are unique in their self-assembly, formation of robust materials in the form of fibers, films and 3D matrices, and are polymorphic (the structure can be controlled among many assembly states). For example, silk fibers are the strongest known fibers and rival even high performance fibers. They are also effective in resisting compression. In 3D porous matrices the compressive resistance exceeds other commonly used organic polymers as biomaterial matrices. Inorganic domains, including silica and hydroxyapatite are prominent in biological systems as key inorganic components found associated with proteins. These mineral phases dominate skeletal components of most systems.

The fibrous protein domain can include short to long versions, with the size in part influencing the scale of the composite from the nano to the macro level. For example, the size can range from a single sized hydrophobic block of 50 amino acids, up to multiple blocks as large as desired including up to proteins of sizes in the 100,000 s of Daltons. In addition, the fibrous protein fusion domain could include other proteins such as collagens, coiled-coiled leucine zipper proteins, elastins, keratins, actins, and tubulins.

The silk protein suitable for use in the present invention is preferably fibroin or related proteins (i.e., silks from spiders). The silkworm silk is obtained, for example, from *Bombyx mori*. Spider silk may be obtained from *Nephila clavipes* See, for example, WO 97/08315 and U.S. Pat. No. 5,245,012.

Inorganic Domains/Mineralizing Domains

Mineralizing domains include those that can induce the formation of hydroxyapatite (Example 1), silica (Example 2), cadmium sulfide, and magnetite. In one embodiment, a mineralizing domain that can induce hydroxyapatite nucleation is obtained from dentin matrix protein 1 or bone sialoprotein (G. He, T. Dahl, A. Veis and A. George. Connective Tissue Res. 2003, 44 (Suppl. 1): 240-245; and G. He, T. Dahl, A. Veis and A. George. Nature materials. 2003, 2(8): 552-558; Stubbs et al. J Bone Miner Res. 1997 August; 12(8):1210-22). The full molecule or a minimum portion that can induce mineralization can be used, for example, a 37 amino acid segment from DMP (C-terminus) will induce controlled mineralization of hydroxyapatite. In one example, the mineralization domains were fused to a sequence derived from spider silk having the following silk fibrous domain repeated 15 times (SGRG-GLGGQGAGAAAAAGGAGQGGYGGLGSQGT) (SEQ ID NO: 1) in order to generate functional recombinant silks that possess both robust mechanical properties of the spider silk and the ability to promote mineralization. The recombinant proteins were cloned in pET21a(+) vector and expressed in *E. coli*. As demonstrated below, the identities of these recombinant silks were confirmed by amino acid composition analysis and the mineralization study was carried out on the surfaces of the cast functional recombinant silk films using recombinant protein containing only spider silk sequence as control. It was demonstrated that the functional recombinant silks exhibit an ability to promote the nucleation of hydroxyapatite. The functional recombinant silks (silk fusion proteins) of the present invention have potential application in biomaterials, tissue engineering, advanced material composites and biosensors.

Preferably, the mineralizing domain is capable of inducing the formation of hydroxyapatite, silica, cadmium sulfide, magnetite and other metal salts pending choice of peptide domain utilized.

Preferred mineralizing domains include, for example, dentin matrix protein 1 (DMP1), bone sialoprotein, and fragments of these proteins, and the 19 amino-acid R5 peptide (SEQ ID NO: 17) of the Sil1 protein.

Alternative fibrous proteins and mineralizing domains can also be included in this system using the template provided. For example, peptides identified from other native proteins or identified by combinatorial screening methods can be used. Screening methods can involve any mineralization assay known in the art, for example the hydroxyapatite and silicification assays described herein.

Preparation of Fusion Proteins; Vectors, Host Cells and Expression

The fusion proteins containing a mineralization domain and a fibrous protein domain can be made using standard molecular biology methods well known to those skilled in the art (See for example, Sambrook et al., *Molecular Biology: A laboratory Approach*, Cold Spring Harbor, N.Y. 1989; Ausubel, et al., *Current protocols in Molecular Biology*, Greene Publishing, Y, 1995).

In some embodiments, the fusion proteins of the invention are made using linker sequences. As used herein, the term "linker sequence" refers to a short (e.g., about 1-20 amino acids) sequence of amino acids that is not part of the sequence of either of two polypeptides being joined. For example, a linker sequence is attached on its amino-terminal end to one polypeptide or polypeptide domain and on its carboxyl-terminal end to another polypeptide or polypeptide domain.

The manipulation of nucleic acids that encode the protein domains in the present invention is typically carried out in recombinant vectors. Herein, both phagemid and non-phagemid vectors can be used. As used herein, vector refers to a discrete element that is used to introduce heterologous DNA into cells for the expression and/or replication thereof. Methods by which to select or construct and, subsequently, use such vectors are well known to one of skill in the art. Numerous vectors are publicly available, including bacterial plasmids, bacteriophage, artificial chromosomes, episomal vectors and gene expression vectors. A vector of use according to the invention may be selected to accommodate a polypeptide coding sequence of a desired size. A suitable host cell is transformed with the vector after in vitro cloning manipulations. Host cells may be prokaryotic, such as any of a number of bacterial strains, or may be eukaryotic, such as yeast or other fungal cells, insect or amphibian cells, or mammalian cells including, for example, rodent, simian or human cells. Each vector contains various functional components, which generally include a cloning (or "polylinker") site, an origin of replication and at least one selectable marker gene. If given vector is an expression vector, it additionally possesses one or more of the following: enhancer element, promoter, transcription termination and signal sequences, each positioned in the vicinity of the cloning site, such that they are operatively linked to the gene encoding a polypeptide repertoire member according to the invention.

Both cloning and expression vectors generally contain nucleic acid sequences that enable the vector to replicate in one or more selected host cells. Typically in cloning vectors, this sequence is one that enables the vector to replicate independently of the host chromosomal DNA and includes origins of replication or autonomously replicating sequences. Such sequences are well known for a variety of bacteria, yeast and viruses. For example, the origin of replication from the plasmid pBR322 is suitable for most Gram-negative bacteria, the 2 micron plasmid origin is suitable for yeast, and various viral origins (e.g. SV 40, adenovirus) are useful for cloning vectors in mammalian cells. Generally, the origin of replication is not needed for mammalian expression vectors unless these are used in mammalian cells able to replicate high levels of DNA, such as COS cells.

Advantageously, a cloning or expression vector may contain a selection gene also referred to as a selectable marker. This gene encodes a protein necessary for the survival or growth of transformed host cells grown in a selective culture medium. Host cells not transformed with the vector containing the selection gene will therefore not survive in the culture medium. Typical selection genes encode proteins that confer resistance to antibiotics and other toxins, e.g. ampicillin, neomycin, methotrexate or tetracycline, complement auxotrophic deficiencies, or supply critical nutrients not available in the growth media.

Since the replication of vectors according to the present invention is most conveniently performed in *E. coli* (e.g., strain TB1 or TG1), an *E. coli*-selectable marker, for example, the β-lactamase gene that confers resistance to the antibiotic ampicillin, is of use. These can be obtained from *E. coli* plasmids, such as pBR322 or a pUC plasmid such as pUC18 or pUC19, or pUC119.

Expression vectors usually contain a promoter that is recognized by the host organism and is operably linked to the coding sequence of interest. Such a promoter may be inducible or constitutive. The term "operably linked" refers to a juxtaposition wherein the components described are in a relationship permitting them to function in their intended manner. A control sequence "operably linked" to a coding sequence is ligated in such a way that expression of the coding sequence is achieved under conditions compatible with the control sequences.

Promoters suitable for use with prokaryotic hosts include, for example, the β-lactamase and lactose promoter systems, alkaline phosphatase, the tryptophan (trp) promoter system and hybrid promoters such as the tac promoter. Promoters for use in bacterial systems will also generally contain a Shine-Delgarno sequence operably linked to the coding sequence. Preferred promoters for use in the present invention are the isopropylthiogalactoside (IPTG)-regulatable promoters.

In one preferred embodiment of the invention, the fusion protein of the invention further comprises a tag, e.g. Flag, His, Myc, HA, VSV, or V5, to aid in purification of the protein by standard means. After purification, the fusion protein can be lyophilized or suspended in aqueous solution for preparation of silk materials, such as films, foams or fibers.

Formation of Silk Fibers, Films, Foams and Gels Using the Silk Fusion Protein of the Invention.

The silk fusion proteins of the invention can be processed into films, foams or fibers. As used herein, "silk fibroin" or "silk protein" refers to a silk fusion protein of the invention.

Fibers can be formed by electrospinning. Electrospinning can be performed by any means known in the art (see, for example, U.S. Pat. No. 6,110,590). Preferably, a steel capillary tube with a 1.0 mm internal diameter tip is mounted on an adjustable, electrically insulated stand. Preferably, the capillary tube is maintained at a high electric potential and mounted in the parallel plate geometry. The capillary tube is preferably connected to a syringe filled with silk/biocompatible polymer solution. Preferably, a constant volume flow rate is maintained using a syringe pump, set to keep the solution at the tip of the tube without dripping. The electric potential, solution flow rate, and the distance between the capillary tip and the collection screen are adjusted so that a stable jet is obtained. Dry or wet fibers are collected by varying the distance between the capillary tip and the collection screen.

A collection screen suitable for collecting silk fibers can be a wire mesh, a polymeric mesh, or a water bath. Alternatively and preferably, the collection screen is an aluminum foil. The aluminum foil can be coated with Teflon fluid to make peeling off the silk fibers easier. One skilled in the art will be able to readily select other means of collecting the fiber solution as it travels through the electric field. As is described in more detail in the Examples section below, the electric potential difference between the capillary tip and the aluminum foil counter electrode is, preferably, gradually increased to about 12 kV, however, one skilled in the art should be able to adjust the electric potential to achieve suitable jet stream.

The process of the present invention may further comprise steps of immersing the spun fiber into an alcohol/water solution to induce crystallization of silk. The composition of alcohol/water solution is preferably 90/10 (v/v). The alcohol is preferably methanol, ethanol, isopropyl alcohol (2-propanol) or n-butanol. Methanol is most preferred. Additionally, the process may further comprise the step of washing the fibroin fiber in water.

In another embodiment, the biomaterial is a film. The process for forming the film comprises, for example, the steps of (a) preparing an aqueous silk fibroin solution comprising silk protein; (b) adding a biocompatible polymer to the aqueous solution; (c) drying the mixture; and (d) contacting the dried mixture with an alcohol (preferred alcohols are listed above) and water solution to crystallize a silk blend film. Preferably, the biocompatible polymer is poly(ethylene oxide) (PEO). The process for producing the film may further include step (e) of drawing or mono-axially stretching the resulting silk blend film to alter or enhance its mechanical properties. The stretching of a silk blend film induces molecular alignment in the fiber structure of the film and thereby improves the mechanical properties of the film.

In a further embodiment, the biomaterial is a foam. Foams may be made from methods known in the art, including, for example, freeze-drying and gas foaming in which water is the solvent or nitrogen or other gas is the blowing agent, respectively.

In one embodiment, the foam is a micropatterned foam. Micropatterned foams can be prepared using, for example, the method set forth in U.S. Pat. No. 6,423,252, the disclosure of which is incorporated herein by reference.

Formation of Organic-Inorganic Composites

The claimed invention provides a method for forming an organic-inorganic composite material. The method comprises contacting a template (such as recombinant silk films, sponges or fibers) formed from a fusion polypeptide of the invention with a suitable inorganic material for a sufficient period of time to allow mineralization of the inorganic material. Mineralized material is deposited onto the silk forming an inorganic coating on the template.

The procedure for mineralization of the coating is dependent upon the mineralization domain that is part of the fusion polypeptide of the invention. For example, the mineralizing domain of dentin matrix protein 1 (DMP1), an acidic phosphoprotein secreted into the extracellular matrix during the formation and mineralization of bone and dentin, is involved in the precipitation of hydroxyapatite, the main inorganic component in calcified hard tissue such as bone and teeth of vertebrates (Koutsopoulos, S. *J Biomed Mater Res.* 2002, 62: 600-612). Further, the mineralizing domain of Silaffin protein is involved in the precipitation of silica.

Those in the art are skilled to select the appropriate buffer for precipitation of inorganic material. The formation of inorganic coatings is further described in Examples 1 and 2.

The biomaterial products produced by the processes of the present invention may be used in a variety of medical applications such as wound closure systems, including vascular wound repair devices, hemostatic dressings, patches and glues, sutures, drug delivery and in tissue engineering applications, such as, for example, scaffolding, ligament prosthetic devices and in products for long-term or bio-degradable implantation into the human body. A preferred tissue engineered scaffold is a non-woven network of electrospun fibers.

Additionally, these biomaterials can be used for organ repair replacement or regeneration strategies that may benefit from these unique scaffolds, including but are not limited to, spine disc, cranial tissue, dura, nerve tissue, liver, pancreas, kidney, bladder, spleen, cardiac muscle, skeletal muscle, tendons, ligaments and breast tissues.

In another embodiment of the present invention, silk biomaterials can contain therapeutic agents. To form these materials, the polymer would be mixed with a therapeutic agent prior to forming the material or loaded into the material after it is formed. In addition, the agent can be incorporated into the inorganic coating formed by the silk fusion protein mineralization domain by mixing it with the mineralization solution. The variety of different therapeutic agents that can be used in conjunction with the biomaterials of the present invention is vast. In general, therapeutic agents which may be administered via the pharmaceutical compositions of the invention include, without limitation: antiinfectives such as antibiotics and antiviral agents; chemotherapeutic agents (i.e. anticancer agents); anti-rejection agents; analgesics and analgesic combinations; anti-inflammatory agents; hormones such as steroids; growth factors (bone morphogenic proteins (i.e. BMP's 1-7), bone morphogenic-like proteins (i.e. GFD-5, GFD-7 and GFD-8), epidermal growth factor (EGF), fibroblast growth factor (i.e. FGF 1-9), platelet derived growth factor (PDGF), insulin like growth factor (IGF-I and IGF-II), transforming growth factors (i.e. TGF-.beta.I-III), vascular endothelial growth factor (VEGF)); and other naturally derived or genetically engineered proteins, polysaccharides, glycoproteins, or lipoproteins. These growth factors are described in The Cellular and Molecular Basis of Bone Formation and Repair by Vicki Rosen and R. Scott Thies, published by R. G. Landes Company hereby incorporated herein by reference.

Silk biomaterials containing bioactive materials may be formulated by mixing one or more therapeutic agents with the polymer used to make the material. Alternatively, a therapeutic agent could be coated on to the material preferably with a pharmaceutically acceptable carrier. Any pharmaceutical carrier can be used that does not dissolve the foam. The therapeutic agents, may be present as a liquid, a finely divided solid, or any other appropriate physical form. Typically, but optionally, the matrix will include one or more additives, such as diluents, carriers, excipients, stabilizers or the like.

The amount of therapeutic agent will depend on the particular drug being employed and medical condition being treated. Typically, the amount of drug represents about 0.001 percent to about 70 percent, more typically about 0.001 percent to about 50 percent, most typically about 0.001 percent to about 20 percent by weight of the material. Upon contact with body fluids the drug will be released.

The biocompatible polymer may be extracted from the biomaterial prior to use. This is particularly desirable for tissue engineering applications. Extraction of the biocompatible polymer may be accomplished, for example, by soaking the biomaterial in water prior to use.

The tissue engineering scaffolds biomaterials can be further modified after fabrication. For example, the scaffolds can be coated with bioactive substances that function as receptors or chemoattractors for a desired population of cells. The coating can be applied through absorption or chemical bonding.

Additives suitable for use with the present invention include biologically or pharmaceutically active compounds. Examples of biologically active compounds include cell attachment mediators, such as the peptide containing variations of the "RGD" integrin binding sequence known to affect cellular attachment, biologically active ligands, and substances that enhance or exclude particular varieties of cellular or tissue ingrowth. Such substances include, for example, osteoinductive substances, such as bone morphogenic proteins (BMP), epidermal growth factor (EGF), fibroblast growth factor (FGF), platelet-derived growth factor (PDGF), vascular endothelial growth factor (VEGF), insulin-like growth factor (IGF-I and II), TGF- and the like.

The scaffolds are shaped into articles for tissue engineering and tissue guided regeneration applications, including reconstructive surgery. The structure of the scaffold allows generous cellular ingrowth, eliminating the need for cellular pre-seeding. The scaffolds may also be molded to form external scaffolding for the support of in vitro culturing of cells for the creation of external support organs.

The scaffold functions to mimic the extracellular matrices (ECM) of the body. The scaffold serves as both a physical support and an adhesive substrate for isolated cells during in vitro culture and subsequent implantation. As the transplanted cell populations grow and the cells function normally, they begin to secrete their own ECM support.

In the reconstruction of structural tissues like cartilage and bone, tissue shape is integral to function, requiring the molding of the scaffold into articles of varying thickness and shape. Any crevices, apertures or refinements desired in the three-dimensional structure can be created by removing portions of the matrix with scissors, a scalpel, a laser beam or any other cutting instrument. Scaffold applications include the regeneration of tissues such as nervous, musculoskeletal, cartilaginous, tendenous, hepatic, pancreatic, ocular, integumenary, arteriovenous, urinary or any other tissue forming solid or hollow organs.

The scaffold may also be used in transplantation as a matrix for dissociated cells, e.g., chondrocytes or hepatocytes, to create a three-dimensional tissue or organ. Any type of cell can be added to the scaffold for culturing and possible implantation, including cells of the muscular and skeletal systems, such as chondrocytes, fibroblasts, muscle cells and osteocytes, parenchymal cells such as hepatocytes, pancreatic cells (including Islet cells), cells of intestinal origin, and other cells such as nerve cells, bone marrow cells, skin cells and stem cells, and combination thereof, either as obtained from donors, from established cell culture lines, or even before or after genetic engineering. Pieces of tissue can also be used, which may provide a number of different cell types in the same structure.

The cells are obtained from a suitable donor, or the patient into which they are to be implanted, dissociated using standard techniques and seeded onto and into the scaffold. In vitro culturing optionally may be performed prior to implantation. Alternatively, the scaffold is implanted, allowed to vascularize, then cells are injected into the scaffold. Methods and reagents for culturing cells in vitro and implantation of a tissue scaffold are known to those skilled in the art.

The biomaterials of the claimed invention may be sterilized using conventional sterilization process such as radiation based sterilization (i.e. gamma-ray), chemical based sterilization (ethylene oxide) or other appropriate procedures. Preferably the sterilization process will be with ethylene oxide at a temperature between 52-55° C. for a time of 8 hours or less. After sterilization the biomaterials may be packaged in an appropriate sterilize moisture resistant package for shipment and use in hospitals and other health care facilities.

The invention will be further characterized by the following examples which are intended to be exemplary of the invention.

EXAMPLES

Example 1

Formation of Hydroxyapatite Silk Fusions

Hydroxyapatite (HAP, $Ca_5(PO_4)_3(OH)$) is the most stable calcium phosphate salt at normal temperature and pH between 4 and 12 (Aaron, S. Posner *Physiological review,* 1969, 49(4): 760-792). Hydroxyapatite is the main inorganic component in calcified hard tissue such as bone and teeth of vertebrates (Koutsopoulos, S. *J Biomed Mater Res.* 2002, 62: 600-612). In addition, hydroxyapatite also has many applications in protein chromatography, water treatment processes, fertilizer and pharmaceutical products (Bailliez, S.; Nzihou, A.; Beche, E.; Flamant, G. *Process Safety and Environmental Protection,* 2004, 82(B2): 175-180). For calcified hard tissue, hydroxyapatite contributes to its stiffness, while organic matrix contributes to its plasticity (Landis, W. J. *Bone,* 16(5): 533-544). The inherent strength and other mechanical properties of the skeletal system are thought to depend on an interaction between its organic and inorganic matrix strength, here hydroxyapatite. One example is the composite formed between the normal mineral salt, hydroxyapatite, and collagen, the principal organic component of the vertebrate skeleton, able to resist a wide range of compressive or tensile forces whereas either material alone can not (Chen, Q. Z.; Wong, C. T.; Lu, W. W.; Cheung, K. M. C.; Leong, J. C. Y. and Luk, K. D. K. *Biomaterials,* 2004, 25: 4243-4254). In the present disclosure, we demonstrate a proof of concept with dental matrix protein (DMP).

Dentin matrix protein 1 (DMP1) is an acidic phosphoprotein secreted into the extracellular matrix during the formation and mineralization of bone and dentin, therefore, it is believed that DMP1 plays an important role in the initiation of mineralization (J. Q. Feng, H. Huang, Y. Lu, L. Ye, Y. Xie, T. W. Tsutsui, T. Kunieda, T. Castranio, G. Scott, L. B. Bonewald, and Y. Mishina. *J Dent Res.* 2003, 82(10): 776-780; W. T. Butler, H. Ritchie. *Int J Dev Biol,* 1995, 39: 169-179; George, B. Sabsay, P. A. L. Simonian, and A. Veis. *J Biol Chem,* 1993, 268(17):12624-12630). It has been reported that DMP1 nucleates the formation of hydroxyapatite in vitro (G. He, T. Dahl, A. Veis and A. George. *Connective Tissue Res.* 2003, 44 (Suppl. 1): 240-245; and G. He, T. Dahl, A. Veis and A. George. *Nature materials.* 2003, 2(8): 552-558) by binding calcium ions and initiating mineral deposition. It has also been reported that DMP1 binds to the N-telopeptide region of type I collagen and the collagen-binding domains involved in this interaction have been identified (G. He and A. George. *J Biol. Chem.* 2004, 279(12): 11649-11656).

We generated various fibrous protein domain-mineralizing domain fusion proteins. See for example FIGS. 1-5. FIG. 2 shows the sequence of CRGD-15mer-CDMP1 (SEQ ID NO: 9), a fusion protein of a spider silk fibrous protein domain ((CRGD-15mer) (See, SEQ ID NO: 5), which is indicated by a dark grey highlight, and the C-terminal end of DMP1 mineralizing domain (See, SEQ ID NO: 6), which is indicated with light grey highlight.

FIG. 3 shows the sequence of the fusion protein CRGD-15mer-DMP1 (SEQ ID NO: 10). CRGD-15mer-DMP1 (SEQ ID NO: 10) is a fusion protein of spider silk fibrous protein domain ((CRGD-15mer) (See, SEQ ID NO: 5), which is indicated by a dark grey highlight, and the full length sequence of DMP1 mineralizing domain (See, SEQ ID NO: 7), which is indicated with light grey highlight.

FIG. 4 shows the sequence of the fusion protein 15mer-BSP (SEQ ID NO: 11). 15mer-BSP (SEQ ID NO: 11) is a fusion protein of spider silk fibrous protein domain ((15mer) (See, SEQ ID NO: 4), which is indicated by light grey highlight, and a mineralizing domain of bone sialoprotein (BSP) (SEQ ID NO: 8), which is indicated with dark grey highlight.

FIG. 5 shows the sequence of the fusion protein CRGD-15mer-BSP (SEQ ID NO: 12). CRGD-15mer-BSP (SEQ ID NO: 12) a fusion protein of spider silk fibrous protein domain ((CRGD-15mer) (See, SEQ ID NO: 5), which is indicated by light grey highlight, and a mineralizing domain of bone sialoprotein (BSP) (SEQ ID NO: 8), which is indicated with dark grey highlight.

Construction of Expression Vector for Recombinant Spider Silks: The consensus repeat unit of spider silk (-SGRGGLGGQGAGAAAAAGGAGQGGY GGLGSQGT-) (SEQ ID NO: 1) was derived from the native sequence of the spidroin 1 of *N. clavipes* (accession P19837). The construction of the expression vector pET30a (+) containing 15 repeats of the silk was previously described (Bini et al., 2005) and was termed pET30a (+)-15mer. Plasmid containing the rat dentin matrix protein 1 cDNA (pGEX-DMP1) was previously described (Feng et al., J. Dent. Res. 2003, 82(10):776-780). Primers with BamHI and XhoI restriction enzyme sites were designed in order to copy the C-terminal portion of rat DMP1 from pGEX-DMP1 by PCR: BamH I site, C-DMP1f: 5'-CAGGATCCAGGGGTGACAACCCAGAT-3' (SEQ ID NO: 26) and Xho I site, C-DMP1r: 5'-GCC TCGAGGTAGCCATCTTGGCAATC-3' (SEQ ID NO: 27). PCR products were double digested with BamHI and XhoI before running on a 1% agarose gel. The band of C-terminal DMP1 DNA were cut from gel and purified using a MinElute gel extraction kit. Expression vector pET21a (+) was also double digested with BamHI and XhoI before running on a 0.8% agarose gel. The band of linearized pET21a (+) was purified using a QIAquick gel extraction kit. After determining the DNA concentration of the vector pET21a (+) and insert of C-terminal DMP1 based on intensities of 1 µl of each in a 1% gel against 1 µl of high mass DNA ladder, the ligation reactions were performed using a Quick ligation Kit™ based on an insert to vector molar ratio of 5:1. Fifty µl of one Shot® Mach1™ T1 phage-resistant cells were transformed with 1 µl of ligation reaction. The correct clone of vector pET21a (+) containing C-terminal DMP1, named as pET21a (+)-CDMP1 was determined by DNA sequencing with forward and reverse T7 primers. pET21a (+)-CDMP1 was digested with BamHI and dephosphorylated with CIP before running on 0.8% agarose gel. The linearized vector was purified using a QIAquick gel extraction kit. pET30a (+)-15mer was digested with BamHI before running on 1% agarose gel and the DNA encoding the 15 repeat unit of spider silk was purified using a MinElute gel extraction kit. The DNA concentrations of the vector pET21a (+)-CDMP1 and the insert: spider silk 15 mer were determined using the same method as described above. The spider silk 15 mer was then inserted into pET21a (+)-CDMP1 at the BamHI site by ligation reaction and the resulting vector was named as pET21a (+)-SS15m-CDMP1. DNA sequencing with forward and reverse T7 primers was performed to check the sequences of the vector.

Protein Expression and Purification: Expression plasmid pET21a (+)-SS15m-CDMP1 was transformed into *Escherichia coli* RY-3041 strain, kindly provided by Professor Ry Young (Texas A&M University, College Station, Tex.). High cell density cultivation using a 1.25 liter jar fermentor (Bioflo 3000; New Brunswick Scientific Co., Edison, N.J.) was performed as described previously (Butler et al. Int. J. Dev. Biol. 1995, 39: 169-179). Expression was induced by adding isopropyl-β-D-thiogalactoside to a final concentration of 2 mM at the early log phase when $A_{600}$ was about 30. Cells were harvested after 3 h of induction by centrifuging the culture at 4° C., 6000×g, for 10 min. The cells were then sonicated on ice using sonicator equipped with a microtip. Ten second burst at 100 W with a 10 second cooling period between each burst was applied. The lysate was centrifuged at 10,000×g for 30 min at 4° C. to pellet the cellular debris. The recombinant silk protein was purified using Ni-NTA agarose resin from supernatant at 4° C. The purification fractions that contain the target protein were dialyzed against distilled water for 2 days and dry proteins were prepared by lyophilizing the aqueous solution. Dialyzed purification fractions were also concentrated and desalted by using Centricon plus 70 (NMW=10 kDa).

Protein Characterization: SDS-PAGE was performed to analyze purification fractions and Western blot was performed using His-tag monoclonal antibody to further confirm the expression of the target proteins. Western blot analysis of CRGD-15mer-CDMP1 (SEQ ID NO: 9) showed expression of the protein (data not shown). The target protein bands on 4-12% Bis-Tris PAGE gel were analyzed at the Yale University W. M. Keck Biotechnology Resource Laboratory to determine amino acid compositions. A Bruker Proflex™ mass spectrometer (Bruker, Billerica, Mass.) was used for molecular weight determination.

Change of Protein Secondary Structure by Calcium Ion Binding: 0.2 mg/mL protein aqueous solution was prepared by the method described in protein expression and purification. Calcium chloride solution (1M) was added such that a molar ratio of protein to Ca ion was maintained at 1:1000. Protein secondary structures before and after adding Ca ion were studied by Fourier Transform Infrared Spectroscopy (FTIR). FTIR studies were performed using a Bruker Tensor 27 FTIR spectrometer with a BioATR accessory.

Film Formation: Recombinant proteins were dissolved in hexafluoroisopropanol (HFIP) to a final concentration of 2% w/v. One-hundred µl of silk HFIP solution was loaded onto a silica wafer and dried in hood. Dried silk film was treated with 90% methanol to induce the transition of secondary structure from random coil to beta sheet. Concentrated silk aqueous solution was then loaded onto silk film and incubated at 37° C. overnight to dry.

In vitro Mineralization: The silk films formed on silica wafer were then incubated in 1.5× simulated body fluid (SBF). 1.5×SBF was prepared as described previously (3) by dissolving reagent grade $CaCl_2$, $KH_2PO_4$, NaCl, KCl, $MgCl_2.6H_2O$, $NaHCO_3$, $Na_2SO_4$ in distilled water and buffering at pH 7.3 with tris-hydroxymethyl aminomethane and hydrochloric acid (HCl). A 1.5×SBF solution contains 1.5 times higher ion concentration than the SBF solution with ion concentrations close to human blood plasma. Fresh 1.5×SBF was prepared daily to replace the 1.5×SBF. After the silk coated silica wafers were soaked in 1.5×SBF for 3, 7, 14 and 21 days, they were removed, gently rinsed with distilled water and dried at room temperature.

Scanning Electron Microscopy: Morphological investigation of the dried films before and after incubating in 1.5×SBF was performed using LEO 982 Field Emission Scanning Electron Microscope (SEM) (LEO Electron Microscopy, Inc., Thornwood, N.Y.) at 3.0 kV. The sample was sputter coated with gold prior to examination.

Transmission Electron Microscopy: Samples for transmission electron microscopy (TEM) analysis were prepared by ultrasonicating of the silk films after incubation in 1.5×SBF in 200 µL of absolute ethanol for 10 min and then depositing a few drops of the suspension onto a standard TEM copper grid with a holey carbon support film. TEM images were obtained with a JOEL 2100 TEM operating at 200 kV with a $LaB_6$ filament and recorded with a slow scan CCD camera. The diffraction patterns were obtained at calibrated camera lengths using a $NiO_x$ test specimen as a reference.

Results

Protein Expression and Purification: CRGD-15mer (SEQ ID NO: 5), molecular weight of which is 48.56 kDa, migrated to the right position on SDS-PAGE gel, while the apparent molecular weight of CRGD-15mer-CDMP1 (SEQ ID NO: 9)

indicated by SDS-PAGE electrophoresis was higher than the calculated molecular weight, which is 58.89 kDa. This is due to high content of acidic amino acids such as aspartic acid and glutamic acid in CRGD-15mer-CDMP1 (SEQ ID NO: 9). Western blot analysis of CRGD-15mer-CDMP1 (SEQ ID NO: 9) and CRGD-15mer-CDMP1 (SEQ ID NO: 9) was detected based on the His tag (data not shown).

Amino Acid Composition Analysis: Amino acid composition analysis confirmed the correct composition for the purified CRGD-15mer-CDMP1 (SEQ ID NO: 9).

Figure 11:
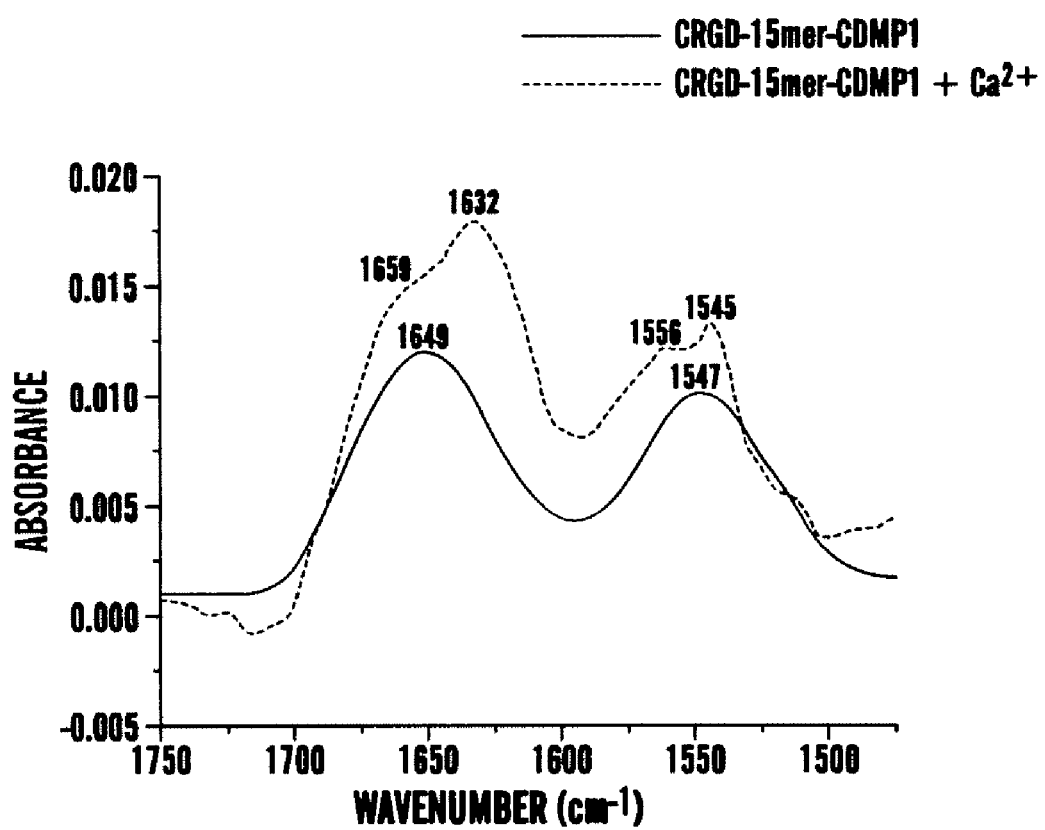
FIG. 11 shows Fourier transform infared spectroscopy (FTIR) analysis of the structure of CRGD-15mer-CDMP1 (SEQ ID NO: 9) before and after Ca ion binding, as described in Example 1.

Functional Change of Protein Secondary Structure by Calcium Ion Binding: CRGD-15mer-CDMP1 (SEQ ID NO: 9) was unordered random coil in water before adding $CaCl_2$, indicated by amide I peak at 1649 $cm^{-1}$ and amide II peak at 1548 $cm^{-1}$. After Ca ion binding, α helix and β sheet structures showed up, demonstrated by amide I peak at 1659 $cm^{-1}$ (α helix) and 1632 $cm^{-1}$ ((β sheet) (FIG. 11).

Figure 12:
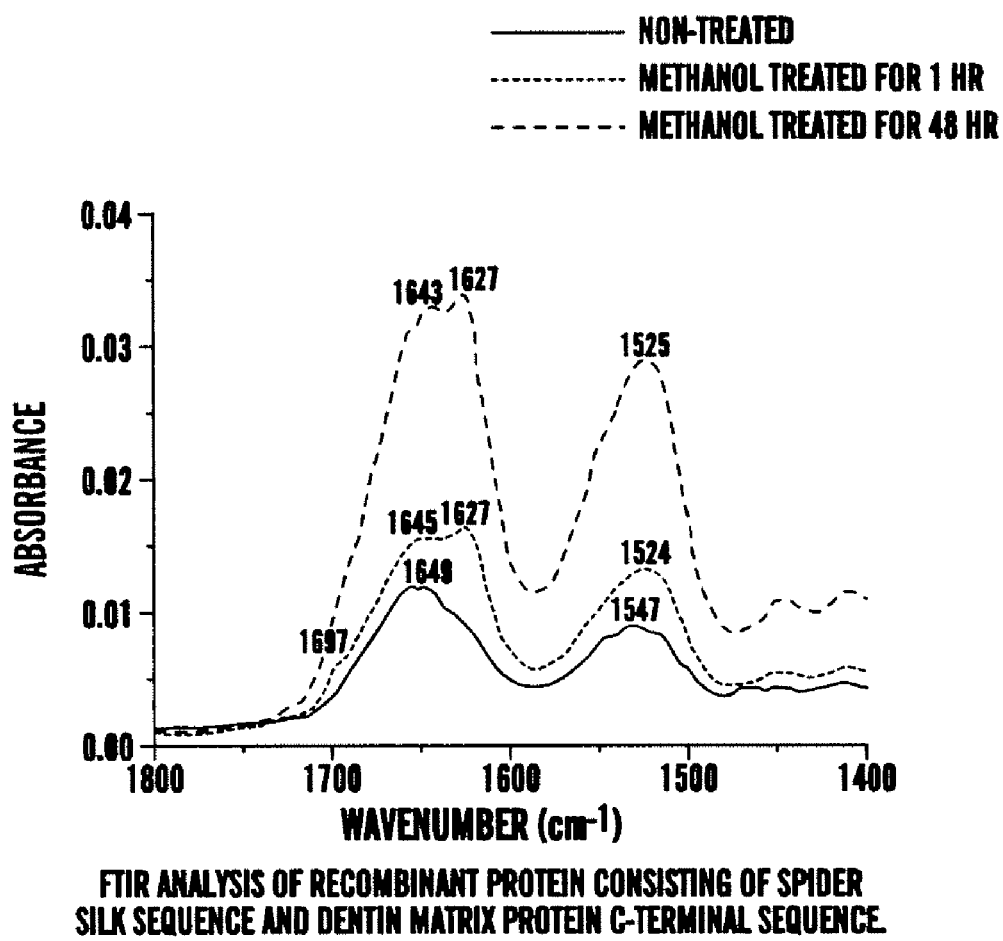
FIG. 12 shows FTIR analysis of structure of CRGD-15mer-CDMP1 (SEQ ID NO: 9) before and after treatment with methanol, as described in Example 1.

Film Formation: Silk secondary structure changed from random coil to β sheet after treated with 90% methanol (FIG. 12) so that the film was more robust in solution.

Functional Assessments of the Fusion Proteins

The apatite nucleation ability of the functional recombinant silks was studied using the method of alternate soaking process. Silk films of the recombinant fusion proteins were cast using standard methods. Lyophilized fusion proteins were dissolved in HFIP solvent at a concentration of 2.5% w/v overnight at 4° C. The silk-HFIP solutions were then pipetted into 24-well culture plates and left in the hood for about 3 hours for the silk films to form and dry out. The silk films were then treated with 90% v/v methanol to induce β-sheet formation and prevent resolubilization of the films in aqueous solutions.

Figure 6B:
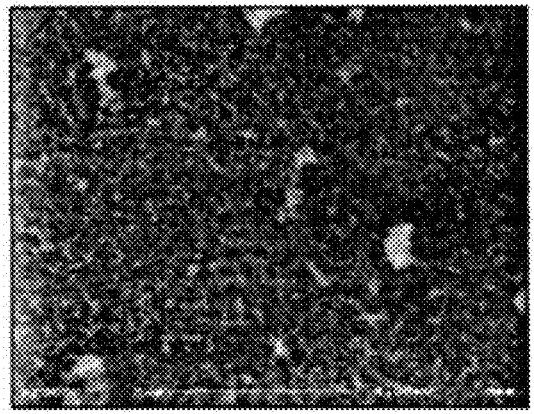
Figure 6C:
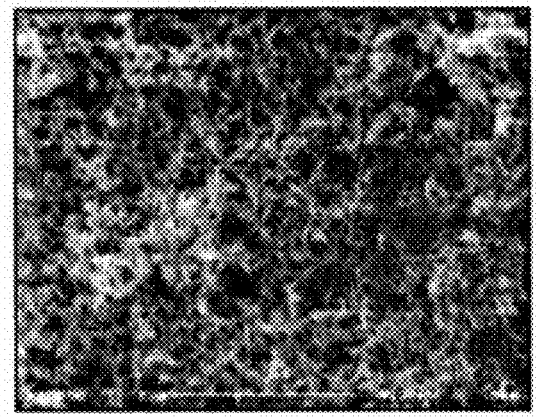

Scanning Electron Microscopy: To asses the ability for mineralization, the cast recombinant silk film was first soaked in 200 mM aqueous calcium chloride solution buffered with tris(hydroxymethyl) aminomethane and HCl (pH 7.4) (Ca solution) for 1 hr at 37° C., then Ca solution was aspirated and the film was washed with abundant distilled water to wash way any unbound $Ca^{2+}$, then 120 mM aqueous disodium hydrogenphosphate (P solution) was added to immerse the silk film for 1 hr at 37° C. After soaking in P solution for 1 hr, the film was washed again by distilled water. This is one round of mineralization. Three rounds of the soaking were carried out. The film surface was then observed by SEM. See FIGS. 6A-6C, which show mineral deposition on silk film cast using CRGD-15mer-CDMP1 (SEQ ID NO: 9). Deposition began to occur as in round one (FIG. 6B) and continued through round three (FIG. 6C). Control films made from CRGD-15mer (SEQ ID NO: 5) and 15mer (SEQ ID NO: 4) showed no deposition (data not shown). The SEM images indicate that the functional fusion silk proteins are capable of inducing apatite nucleation and growth, while silk proteins that so not contain mineralizing domains do not promote apatite nucleation.

In addition, scanning electron microscopy (SEM) surface morphologies of recombinant spider silk films after soaking in 1.5×SBF for various periods of time were assessed see FIG. 13. FIG. 13(A1)-FIG. 13(A5), SS15m-CDMP1 soaked in 1.5×SBF for 0, 3, 7, 14 and 21 days: FIG. 13(A1)-FIG. 13(A5) respectively. FIG. 13(B1)-FIG. 13(B5), SS15m soaked in 1.5×SBF for 0, 3, 7, 14 and 21 days: FIG. 13(B1)-FIG. 13(B5) respectively.

The surfaces of the films made of CRGD-15mer-CDMP1 (SEQ ID NO: 9) and CRGD-15mer (SEQ ID NO: 5) were smooth after casting and there was no big difference between two films (FIG. 13A1 and FIG. 13B1). However, after immersing in 1.5×SBF for 3 days, the surface morphologies of the films were different (FIG. 13A2 and FIG. 13B2).

Figure 14A:
FIGS. 14A to 14C show Transmission Electron Microscopy (TEM) images of crystals grown on CRGD-15mer-CDMP1 (SEQ ID NO: 9) after soaking in 1.5×SBF for 21 days, as described in Example 1.
Figure 14B:
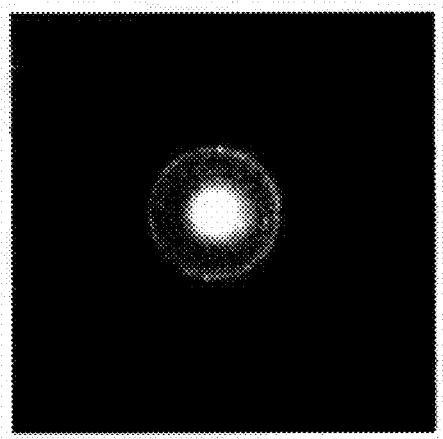
Figure 14C:

Transmission Electron Microscopy: The high-magnification image of the crystals grew on CRGD-15mer-CDMP1 (SEQ ID NO: 9) (FIG. 14A) showed that the apatite, which appeared flake-like in the SEM, is composed of aggregates of nanocrystals with need shapes 100-200 nm in length. The electron diffraction pattern of the nanocrystals (FIG. 14B) showed diffraction rings. The spacings of the rings agreed with the characteristic x-ray diffraction spacing of hydroxyapatite (JCPDS 09-0432). The rings could be assigned to the (002), (211) planes. In addition, a high-resolution TEM image (FIG. 14C) showed the lattice fringes of apatite nanocrystals. The average distance between fringes is 0.82 nm, which is consistent with the value of the (100) inerplanar spacing in the apatite structure (0.817 nm).

Example 2

Formation of Silica Silk Fusions

Introduction

Silica is widespread in biological systems and serves different functions, among which the most essential ones include support and protection in single-celled organisms, such as diatoms, to higher plants and animals. Despite its widespread occurrence and importance of function, little is known about biosilica and the mechanisms used to produce controlled microscopic and macroscopic silica structures with such nanoscale precision and symmetry. The remarkable control in vivo of the morphology of these beautiful intricate patterns at small length scales are species-specific and has attracted a great deal of interest in recent years as these features exceed the capabilities of present-day synthetic and technological approaches to materials engineering in vitro.

Silaffins[1; 2; 3; 4; 5] form part of three families of proteins identified to date in the organic matrix of the cell wall of the diatom *Cylindrotheca fusiformis*. Silaffins are highly post-translationally modified peptides and have received the most attention because of their ability to induce and regulate silica precipitation at ambient temperature and pressure. Silaffins are low-molecular weight polypeptides: natSil-1A (6.5 kDa)[4], natSil-1B (10 kDa)[5], and natSil-2 (40 kDa)[5], isolated by treating the diatom cell wall with ammonium fluoride. A gene sil 1 has been isolated from a *C. fusiformis* genomic library and it encodes a polypeptide of 265 amino acids. Seven repeated sequences were identified in this sequence and named R1 to R7[1]. R1 corresponds to the precursor of Silaffin-1B, while R3 to R7 and R2 correspond to the precursors of the Silaffin-1A1 and Silaffin-1A2, respectively.

Controlled formation of biosilica structures by different proteins and peptides under various physical reaction environments has also been reported[6; 7; 8; 9]. The 19 amino-acid R5 peptide of the Sil1 protein was utilized to obtain silica nanostructures with different morphologies including spheres, arch-shaped morphologies and even elongated fibers[7]. These results suggest that through careful manipulation of the environmental conditions and the application of a linear shear force, distinct morphologies can be attained. These opportunities for control of materials outcomes in biosilica morphology establish important links to device fabrication from these materials with regularity in process and outcomes to achieve technological relevance in the future, such as for silica based micro- and nano-devices.

Applicants have genetically cloned the R5 peptide unit of Sil1 protein to a 15mer spider silk clone of the consensus sequence of the golden orb spider *Nephila clavipes*, expressed the fusion protein and performed the same silicification reactions on silk films made from the expressed protein. The purpose of fusing this silicification-inducing peptide unit to our genetically engineered silk is to combine the properties of our silk whether in the form of films or other such as spun fibers to the silica precipitating properties of R5 under ambient conditions to produce biomaterials with controlled silica morphologies on the surface. These biomaterials are especially useful in such fields as controlled drug delivery.

Materials and Methods

Design and Cloning of Spider Silk Sequences

The repeat unit was selected used in the design of the 15mer (SEQ ID NO: 4) and CRGD15mer (SEQ ID NO: 5) was based on the consensus sequence of spidroin1 native sequence of *Nephila clavipes* (accession P19837) (-SGRG-GLGGQGAGAAAAAGGAGQGGYGGLGSQGT-) (SEQ ID NO: 1). Multimers encoding the repeat were cloned through the transfer of cloned inserts between two shuttle vectors based on pUC19 and pCR-Script (Novagen, Wis.), which were ampicillin and chloramphenicol resistant respectively[10; 11].

The expression vector pET-30a (Novagen, Madison, Wis.) was modified with a linker carrying the SpeI site flanked by sequences encoding the amino acids CRGD (SEQ ID NO: 2) to obtain pET30-link. The two complementary oligonucleotide sequences for the linker were: GGATCCTGTCGCG-GTGACACTAGTCGCGGTGACTGTG (SEQ ID NO: 13) and GGATCCACAGTCACCGCGACTAGTGT-CACCGCGACAG (SEQ ID NO: 14). The restriction sites of BamHI and SpeI are underlined. The 15mer sequence obtained by multimerization was inserted into pET30-link to generate pET30-CRGD15mer. For the production of a spider silk protein without CRGD (SEQ ID NO: 2), the construct pET30-15mer was obtained by subcloning the NcoI-NotI fragment of pCR-15 into pET-30a vector.

To construct the fusion protein CRGD15mer-R5 (SEQ ID NO: 24), the polylinker of pET-21a(+) shuttle vector was redesigned to contain a His-Tag and the CRGD15mer (SEQ ID NO: 5) was digested with the restriction enzyme BamHI from pET-30a vector and inserted into the pET-21a(+)-link vector. Two complementary oligonucleotide sequences for the R5 peptide (SEQ ID NO: 17) were designed with EcoRI and NotI sites at the 5' and 3' ends respectively:

(SEQ ID NO: 15)
5' aattcagcagcaaaaaaagcggcagctattcgggcagcaaaggcag caaacgccgcatcctcgc 3'
and (SEQ ID NO: 16)
3' gtcgtcgttttttcgccgtcgataagccgtcgtttccgtcgttt gcggcgtaggagcgccgg 5'

These synthetic oligonucleotides were annealed and ligated into the pET-21a(+)-link vector right next to the CRGD15mer clone to create the fusion protein with the His-Tag at the C-terminus.

To construct the fusion protein 15mer-R5 (SEQ ID NO: 25), the synthetic oligonucleotides were ligated into the NotI and XhoI restriction sites of pET-21a(+) vector right next to the 15mer clone. This fusion protein has a His-Tag at the N-terminus. The amino acid sequence of the R5 peptide of Sil1 protein is: SSKKSGSYSGSKGSKRRIL (SEQ ID NO: 17). Use of other Sil1 protein sequences are also contemplated, for example, the R2 peptide SSKKSGSYSGYST-KKSGSRRIL (SEQ ID NO: 18), the R3 peptide SSKKSG-SYSGYSKGSKRRIL (SEQ ID NO: 19), the R4/R6 peptide SSKKSGSYSGYSKGSKRRNL (SEQ ID NO: 20), the R1 peptide SSKKSGSYYSYGTKK (SEQ ID NO:21).

Protein Expression and Purification

The constructs pET-21(a)+-15mer-R5 and pET-30a-CRGD15mer-R5 were used to transform the *E. coli* host strains RY-3041, a mutant strain defective in the expression of SlyD protein, for expression[12; 13]. Cells were cultivated in LB broth at 37° C. Protein expression was induced by the addition of 1 mM IPTG (Fisher Scientific, Hampton, N.H.) when the $OD_{600}$ was between 0.6 and 0.8. After approximately 6 hours of protein expression, the cells were harvested by centrifugation at 9500 rpm. For large scale expression, *E. coli* was grown in a fermentor (Bioflo 3000, New Brunswick Scientific Co., Edison, N.J.) in minimal medium supplemented with 1% yeast extract. Ammonia was used as the base to maintain the pH at 6.8. When the pH exceeded 6.88, as a result of glucose exhaustion in the culture, a feed solution (50% glucose, 10% Yeast Extract, 2% $MgSO_4.7H_2O$) was added. Pure $O_2$ was also provided to the culture to sustain the level of dissolved oxygen above 40%. All culture media contained kanamycin (50 μg/ml) or ampicillin (100 μg/ml) for selectivity. For the fermentor grown cells, expression was induced when the absorbance was between 25 and 30 at $OD_{600}$.

The cell pellets were resuspended by adding denaturing buffer (100 mM $NaH_2PO_4$, 10 mM Tris HCl, 8 M urea, pH 8.0) containing 10 mM imidazole. The cells were lysed by stiffing for 30 min and were then centrifuged at 9500 rpm at 4° C. for 30 min. His-tag purification of the proteins was performed by addition of Ni-NTA agarose resin (Qiagen, Valencia, Calif.) to the supernatant (batch purification) under denaturing conditions. After washing the column with denaturing buffer at pH 6.3, the proteins were eluted with denaturing buffer at pH 4.5 (without imidazole).

SDS-polyacrylamide gel electrophoresis (PAGE) was performed using 4-12% precast NuPage Bis-Tris gels (Invitrogen, Carlsbad, Calif.). Electrophoresis was performed in MOPS buffer for 50 min at 200V. Purified samples were extensively dialyzed against several changes of $H_2O$. For dialysis, Snake Skin membranes (Pierce, Rockford, Ill.) with MWCO of 7000 or lower were used. The dialyzed samples were lyophilized using a LabConco lyophilizer. For determination of the amino acid composition, the samples were submitted to the W. M. Keck Foundation Biotechnology Resource Laboratory (Yale University, New Haven, Conn.). The samples were analyzed from bands of interest cut out from the gel or lyophilized powder after purification and dialysis. Determination of protein concentration was performed by BCA assay (Pierce, Rockford, Ill.) or the molar absorptivity at 280 nm. FIGS. 7A and 7B show the sequence of CRGD15mer-R5 (FIG. 7A) and 15mer-R5 (FIG. 7B)

Silicification Reactions

The lyophilized fusion proteins were then dissolved in HFIP solvent at a concentration of 2.5% w/v overnight at 4° C. The silk-HFIP solutions were then pipetted into 24-well culture plates and left in the hood for about 3 hours for the silk films to form and dry out. The silk films were then either left as is or treated with 90% v/v methanol to induce β-sheet formation and prevent resolubilization of the films in aqueous solutions. 100 mM phosphate buffer at pH 5.5 was added to the silk films and leave to sit for about 30 minutes before 1M tetramethoxysilane (TMOS) dissolved in 1 mM hydrochloric acid was added to the mixture for about 10 minutes. The films were then washed with MilliQ water three times and left to dry overnight in the fume hood. These films were then analyzed using a LEO 982 Scanning Electron Microscope at the CIMS facility at Harvard University.

SEM Results

Figure 8:
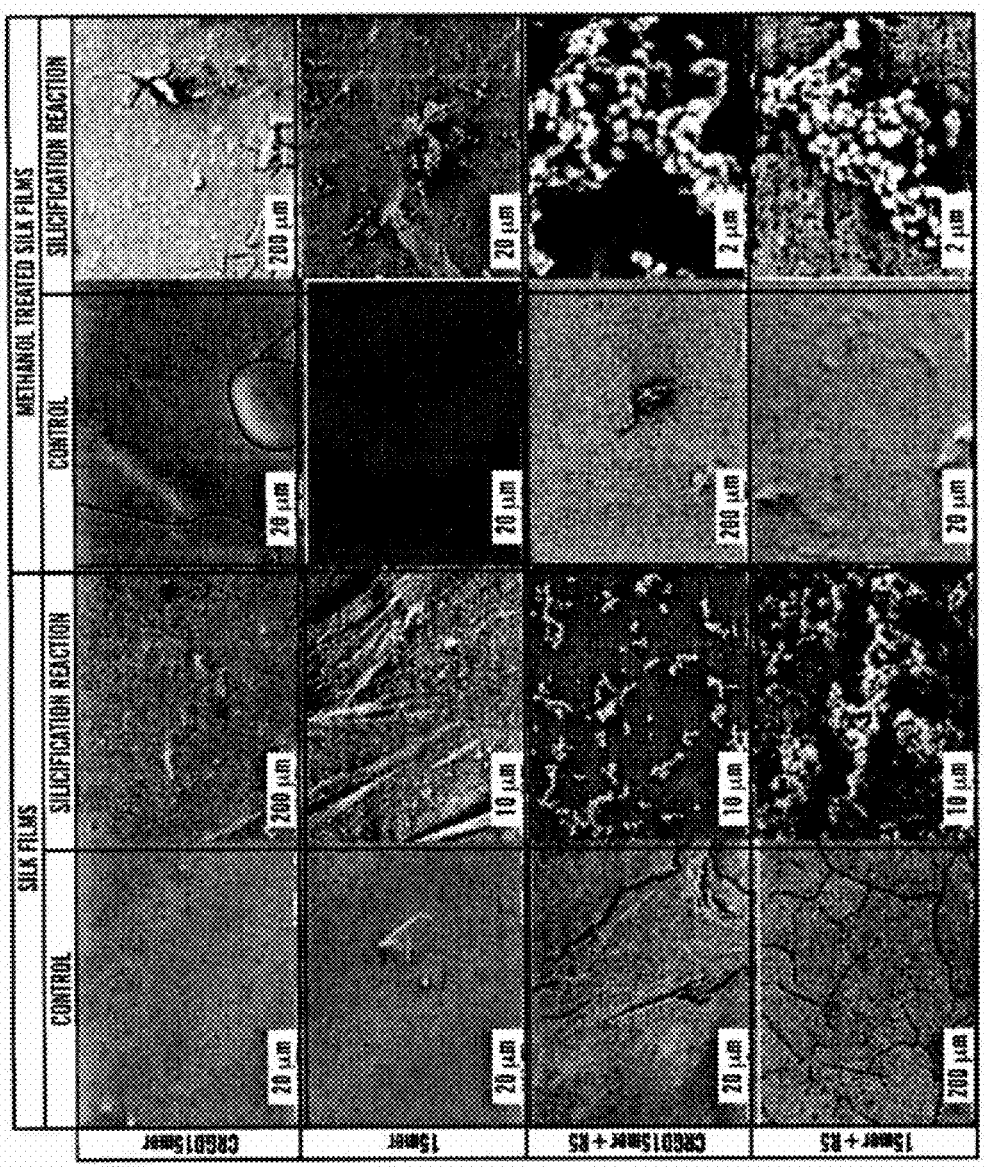
FIG. 8 shows a grid of SEM of untreated and methanol treated silk films formed from the four different genetically engineered silk proteins CRGD15mer (SEQ ID NO: 5), 15mer (SEQ ID NO: 4), CRGD15mer-R5 (SEQ ID NO: 24), and 15mer-R5 (SEQ ID NO: 25) as described in Example 2. Images of the control films and the films that underwent silicification reactions are shown.

In order to exploit the self-assembling properties of silk in developing silk-silica nanocomposites, experiments were performed using TMOS alone as the precursor. Four genetically engineered variants of the spider silk protein (two controls, one with and one without RGD but both without R5 (SEQ ID NO: 17), two chimeric versions of the controls but with R5 (SEQ ID NO: 17)) were cast into films that were either left untreated or were treated with methanol to induce a structural transition to β-sheet and thus decrease film solubility in aqueous buffer. Silicification reactions were performed on the films yielding spherical silica structures with diameters ranging from ~0.5 to 2.0 μm only when the silica precipitating domain, R5 peptide (SEQ ID NO: 17), was fused to the C-terminus of the silk proteins (FIG. 8). The silk proteins that did not contain R5, CRGD15mer (SEQ ID NO: 5) and 15mer (SEQ ID NO: 4), did not yield significant changes in surface morphology of the films upon exposure to the silicification reactions.

Figure 10A:
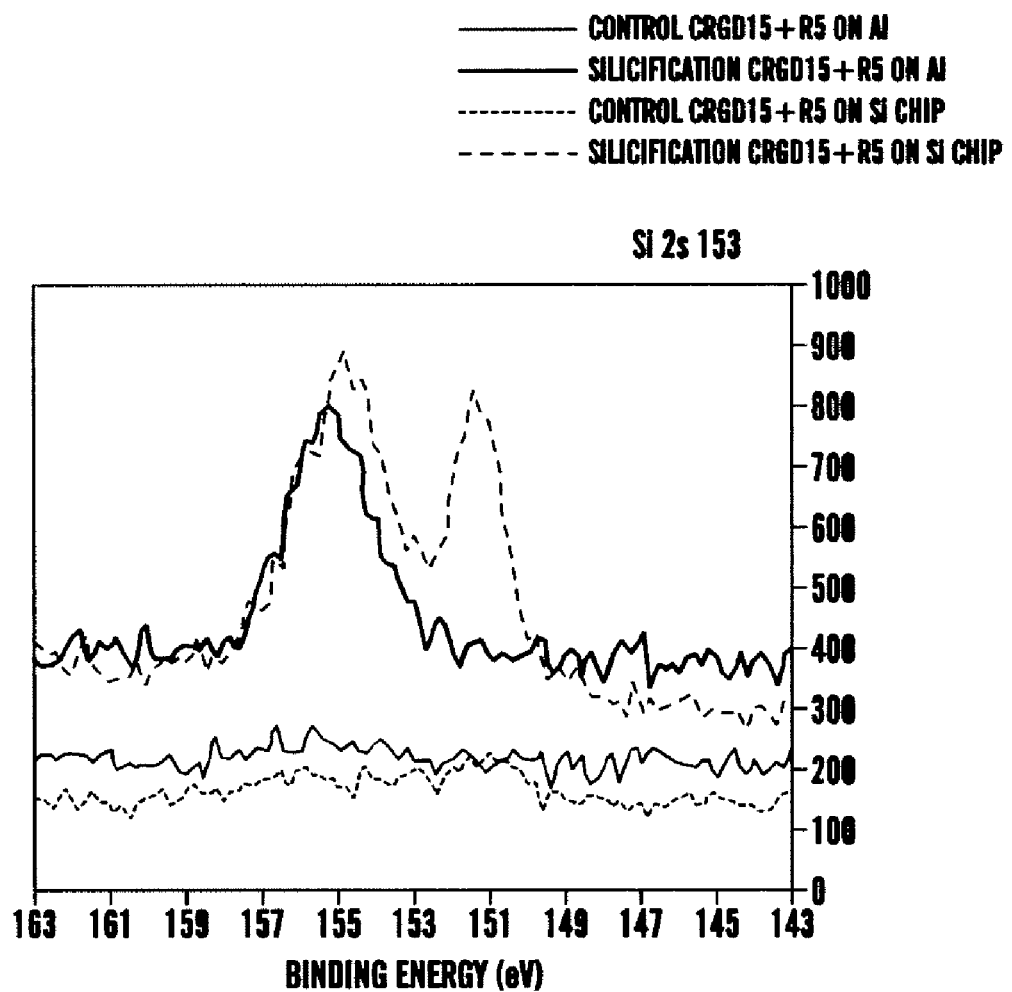
FIGS. 10A to 10B show XPS analysis, as described in Example 2, of CRGD15mer-R5 (SEQ ID NO: 24) and silicified CRGD15mer-R5 (SEQ ID NO: 24) on Al foil and on silicon chip at the characteristic binding energies of (FIG. 10A) 153 eV and (FIG. 10B) 102 eV for electrons found in the 2s and 2p3 electron shells of the silicon atom respectively.
Figure 10B:
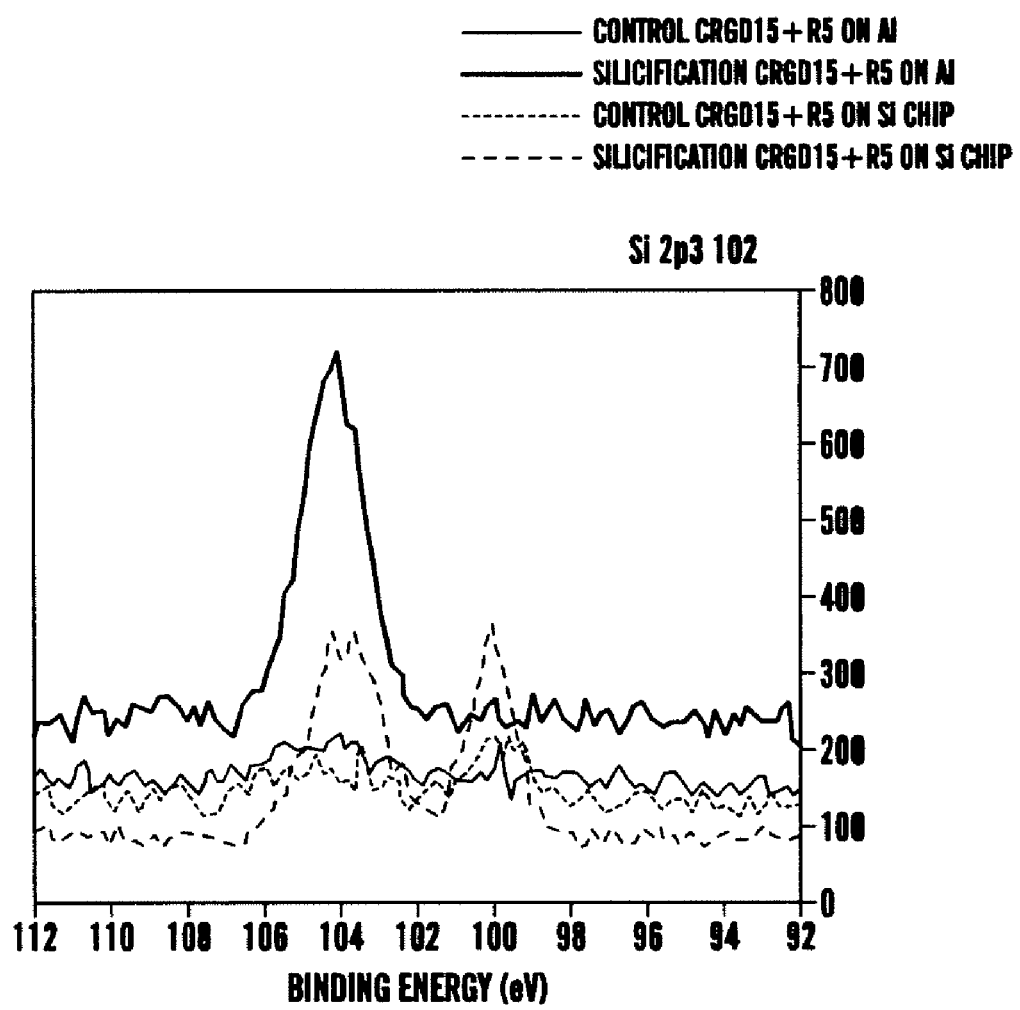

Fusion proteins were assembled into fibers by electrospinning. SEM images of the electropun fibers formed from the chimeric proteins (FIGS. 9A-9E), and the morphological characteristics observed when the fibers were treated with methanol, were similar to those we observed previously for electrospun silk fibroin with polyethylene oxide[15]. Upon silicification on electrospun mats formed from the chimeric protein CRGD15mer+R5 (SEQ ID NO: 24) without methanol treatment, similar spherical silica structures were observed as in the reactions on the cast films. However, the dimensions of the silica spheres were slightly smaller, ranging from 200 to 400 nm (FIGS. 9B and 9C). When the electrospun fibers consisting of the chimera CRGD15mer+R5 (SEQ ID NO: 24) were not treated with methanol, the fibers fused together on the surface. Without the β-sheet inducing methanol treatment, the fibers are prone to partially solubilize on the surface yielding a thin film upon which the mineralization reaction takes place. However, upon treatment of the chimera CRGD15mer+R5 (SEQ ID NO: 24) electrospun mats with methanol before silicification, a thin film formed from the solubilized and then fused fibers at the surface and silica nanospheres did not form as in the sample above. Instead, the fibers fused with each other as expected[15] and although mineralization occurred as confirmed by XPS, silica deposited around the fibers providing a non-uniform coating instead of the spheres (FIGS. 9B and 9C). When the chimera CRGD15mer+R5 (SEQ ID NO: 24) was electrospun during the silica polymerization process (concurrent processing), silica deposition was induced in and on the fibers and elliptically shaped silica particles fused to the fibers were observed (FIGS. 9D and 9E). XPS analysis of the resulting fibers confirmed the presence of elemental silicon (FIG. 10). Thus, the concurrent processing approach, fiber spinning and silicification reactions, resulted in a different morphology of the silica in terms of location within the fibers and shape, compared to the silicification reactions conducted post electrospinning.

Sequences

Fibrous protein domain sequence derived from Spidroin1 (the native sequence of the goldon orb spider *Nephilia clavipes*) SGRGGLGGQGAGAAAAAGGAGQGGYG-GLGSQGT (SEQ ID NO: 1)

A linker sequence CRGD (SEQ ID NO: 2)

The consensus fibrous protein domain sequence derived from Spidroin1 (the native sequence of the goldon orb spider *Nephilia clavipes*) with CRGD linker CRGDTSGRGGLG-GQGAGAAAAAGGAGQGGYGGLGSQGT (SEQ ID NO: 3)

15 mer: An amino acid sequence that contains a repeat of a fibrous protein domain sequence derived from Spidroin1 (the native sequence of the goldon orb spider *Nephilia clavipes*) The fibrous protein domain sequence is repeated 15 times.

(SEQ ID NO: 4)
MASMTGGQQMGRGSAMASGRGGLGGQGAGAAAAAGGAGQGGYGGLGSQ

GTSGRGGLGGQGAGAAAAAGGAGQGGYGGLGSQGTSGRGGLGGQGAGA

AAAAGGAGQGGYGGLGSQGTSGRGGLGGQGAGAAAAAGGAGQGGYGGL

GSQGTSGRGGLGGQGAGAAAAAGGAGQGGYGGLGSQGTSGRGGLGGQG

AGAAAAAGGAGQGGYGGLGSQGTSGRGGLGGQGAGAAAAAGGAGQGGY

GGLGSQGTSGRGGLGGQGAGAAAAAGGAGQGGYGGLGSQGTSGRGGLG

GQGAGAAAAAGGAGQGGYGGLGSQGTSGRGGLGGQGAGAAAAAGGAGQ

GGYGGLGSQGTSGRGGLGGQGAGAAAAAGGAGQGGYGGLGSQGTSGRG

GLGGQGAGAAAAAGGAGQGGYGGLGSQGTSGRGGLGGQGAGAAAAAGG

AGQGGYGGLGSQGTSGRGGLGGQGAGAAAAAGGAGQGGYGGLGSQGTS

GRGGLGGQGAGAAAAAGGAGQGGYGGLGSQGTSHHHHH

CRGD-15mer: an amino acid sequence that contains a repeat of a fibrous protein domain sequence derived from Spidroin1 (the native sequence of the goldon orb spider *Nephilia clavipes*) The fibrous protein domain sequence is repeated 15 times with a CRGD (SEQ ID NO: 2) linking sequence MASMTGGQQMGRGSCRGDTSGRGGLGGQ-GAGAAAAAGGAGQGGYGGLGSQGTSGR GGLGGQ-GAGAAAAAGGAGQGGYGGLGSQGTSGRG-GLGGQGAGAAAAGGAGQGGY GGLGSQGTSGRGGLGGQGAGAAAAAG-GAGQGGYGGLGSQGTSGRGGLGGQGAGAAA AAG-GAGQGGYGGLGSQGTSGRGGLGGQ-GAGAAAAAGGAGQGGYGGLGSQGTSGRG GLGGQGAGAAAAAGGAGQGGYGGLG-SQGTSGRGGLGGQGAGAAAAAGGAGQGGYG GLG-SQGTSGRGGLGGQGAGAAAAAGGAGQG-GYGGLGSQGTSGRGGLGGQGAGAAAA AGGAGQGGYGGLGSQGTSGRGGLGGQ-GAGAAAAAGGAGQGGYGGLGSQGTSGRGGL GGQ-GAGAAAAAGGAGQGGYGGLGSQGTSGRG-GLGGQGAGAAAAAGGAGQGGYGGL GSQGTSGRGGLGGQGAGAAAAAGGAGQG-GYGGLGSQGTSGRGGLGGQGAGAAAAA GGAGQG-GYGGLGSQGTSRGDCGSHHHHHH (SEQ ID NO: 5)

CDMP1, the C-Terminal Sequence of DMP1, a Mineralizing domain RGDNPDNTSQTGDQRDSESSEEDRLNTF-SSSESQSTEEQGDSESNESLSLSEESQESAQDE DSSSQEGLQSQSASRESRSQESQSEED-SRSEENRDSDSQDSSRSKEESNSTGSTSSSEEDN HPKNIEADNRKLIVDAYHNKPIGDQDDNDCQDGY (SEQ ID NO: 6)

DMP1, the full length sequence of DMP1, a Mineralizing domain LPVARYQNTESESSEERTGNLAQSPPPP-MANSDHTDSSESGEELGSDRSQYRPAGGLSKS AGM-DADKEEDEDDSGDDTFGDEDNGPGPEER-QWGGPSRLDSDEDSADTTQSSEDSTSQ ENSAQDTPSDSKDHHSDEADSRPEAGD-STQDSESEEYRVGGGSEGESSHGDGSEFDDEG MQS-DDPGSTRSDRGHTRMSSADISSEESKGD- HEPTSTQDSDDSQDVEFSSRKSFRRSRVS EEDDRGELADSNSRETQSVSTEDFR-SKEESRSETQEDTAETQSQEDSPEGQDPSSESSEEA GEPSQESSSESQEGVASESRGDNP-DNTSQTGDQRDSESSEEDRLNTFSSSESQSTEEQGDS ESNESLSLSEESQESAQD-EDSSSQEGLQSQSASRESRSQESQSEED-SRSEENRDSDSQDSS RSKEESNSTGSTSSSEEDNHP-KNIEADNRKLIVDAYHNKPIGDQDDNDCQDGY (SEQ ID NO: 7)

BSP: Bone sialoprotein, a Mineralizing domain SEFPVQSSSDSSEENGNGDSSEEEEEEEEN-SNEEENNEENEDSDGNED (SEQ ID NO: 8)

CRGD-15mer-CDMP1: (SEQ ID NO: 9): a fusion protein of (SEQ ID NO: 5) and (SEQ ID NO: 6) MASMTG-GQQMGRCRGDTSGRGGLGGQ-GAGAAAAAGGAGQGGYGGLGSQGTSGRGG LGGQ-GAGAAAAAGGAGQGGYGGLGSQGTSGRGGLGGQG AGAAAAAGGAGQGGYGG LGSQGTSGRGGLGGQ-GAGAAAAAGGAGQGGYGGLGSQGTSGRG-GLGGQGAGAAAAA GGAGQGGYGGLGSQGTSGRG-GLGGQGAGAAAAAGGAGQGGYGGLGSQGTSGRGG LG GQGAGAAAAAGGAGQGGYGGLGSQGTSGRGG LGGQGAGAAAAAGGAGQGGYGGLG SQGTSGRG-GLGGQGAGAAAAAGGAGQGGYGGLG-SQGTSGRGGLGGQGAGAAAAAG GAGQGGYGGLG-SQGTSGRGGLGGQGAGAAAAAGGAGQGGYGGLGS QGTSGRGGLGG QGAGAAAAAGGAGQGGYGGLG-SQGTSGRGGLGGQGAGAAAAAGGAGQGGYGGLGS QGTSGRGGLGGQGAGAAAAAGGAGQG-GYGGLGSQGTSGRGGLGGQGAGAAAAAGG AGQG-GYGGLGSQGTSRGDCGSRGDNPDNTSQT-GDQRDSESSEEDRLNTFSSSESQSTEE QGDSESNESLSLSEESQESAQD-EDSSSQEGLQSQSASRESRSQESQSEED-SRSEENRDSDS QDSSRSKEESNSTGSTSSSEEDNHP-KNIEADNRKLIVDAYHNKPIGDQDDNDCQDGY (SEQ ID NO: 9)

CRGD-15mer-DMP1 (SEQ ID NO: 10): a fusion protein of (SEQ ID NO: 5) and SEQ ID NO: 7) MASMTG-GQQMGRCRGDTSGRGGLGGQ-GAGAAAAAGGAGQGGYGGLGSQGTSGRGG LGGQ-GAGAAAAAGGAGQGGYGGLGSQGTSGRGGLGGQG AGAAAAAGGAGQGGYGG LGSQGTSGRGGLGGQ-GAGAAAAAGGAGQGGYGGLGSQGTSGRG-GLGGQGAGAAAAA GGAGQGGYGGLGSQGTSGRG-GLGGQGAGAAAAAGGAGQGGYGGLGSQGTSGRGG LG GQGAGAAAAAGGAGQGGYGGLGSQGTSGRG GL GGQGAGAAAAAGGAGQGGYGGLG SQGTSGRG-GLGGQGAGAAAAAGGAGQGGYGGLG-SQGTSGRGGLGGQGAGAAAAAG GAGQGGYGGLG-SQGTSGRGGLGGQGAGAAAAAGGAGQGGYGGLGS QGTSGRGGLGG QGAGAAAAAGGAGQGGYGGLG-SQGTSGRGGLGGQGAGAAAAAGGAGQGGYGGLGS QGTSGRGGLGGQGAGAAAAAGGAGQG-GYGGLGSQGTSGRGGLGGQGAGAAAAAGG AGQG-GYGGLGSQGTSRGDCGSLPVARYQNTE-SESSEERTGNLAQSPPPPMANSDHTDSS ESGEELGSDRSQYRPAGGLSKSAGMDAD-KEEDEDDSGDDTFGDEDNGPGPEERQWGGP SRLDS-DEDSADTTQSSEDSTSQENSAQDTPSD-SKDHHSDEADSRPEAGDSTQDSESEEYR VGGGSEGESSHGDGSEFDDEGMQSDDPG-STRSDRGHTRMSSADISSEESKGDHEPTSTQ DSDDSQDVEFSSRKSFRRSRVSEED-DRGELADSNSRETQSVSTEDFRSKEESRSETQEDT AETQSQEDSPEGQDPSSESSEE-AGEPSQESSSESQEGVASESRGDNP-DNTSQTGDQRDSES SEEDRLNTFSSSESQSTEEQGD-SESNESLSLSEESQESAQDEDSSSQEGLQSQSASRESR SQESQSEEDSRSEENRDSDSQDSSRSKEESNSTGSTS SSEEDNHPKNIEADNRKLIVDAYHNK PIGDQ DDND-CQDGY (SEQ ID NO: 10)

15mer-BSP (SEQ ID NO: 11): a fusion protein of (SEQ ID NO: 4) and (SEQ ID NO: 8) MASMTGGQQMGRGSA-MASGRGGLGGQGAGAAAAAGGAGQGGYG-GLGSQGTSGRGG LGGQGAGAAAAAGGAGQGGYG-GLGSQGTSGRGGLGGQGAGAAAAAGGAGQGGYGG LGSQGTSGRGGLGGQGAGAAAAAG-GAGQGGYGGLGSQGTSGRGGLGGQGAGAAAAA GGAGQGGYGGLGSQGTSGRGGLGGQ-GAGAAAAAGGAGQGGYGGLGSQGTSGRGGLG GQGAGAAAAAGGAGQGGYGGLGSQGTS-GRGGLGGQGAGAAAAAGGAGQGGYGGLG SQGTS-GRGGLGGQGAGAAAAAGGAGQGGYGGLG-SQGTSGRGGLGGQGAGAAAAAG GAGQGGYGGLGSQGTSGRGGLGGQ-GAGAAAAAGGAGQGGYGGLGSQGTSGRGGLGG QGAGAAAAAGGAGQGGYGGLGSQGTS-GRGGLGGQGAGAAAAAGGAGQGGYGGLGS QGTS-GRGGLGGQGAGAAAAAGGAGQGGYGGLG-SQGTSGRGGLGGQGAGAAAAAGG AGQGGYGGLGSQGTSEFPVQSSSDS-SEENGNGDSSEEEEEEEENSNEEENNEENEDSDG NEDKLHHHHHH (SEQ ID NO: 11)

CRGD-15mer-BSP (SEQ ID NO: 12): a fusion protein of (SEQ ID NO: 5) and (SEQ ID NO: 8) with linker MASMTG-GQQMGRGSCRGDTSGRGGLGGQ-GAGAAAAAGGAGQGGYGGLGSQGTSGR GGLGGQ-GAGAAAAAGGAGQGGYGGLGSQGTSGRGGLGGQG AGAAAAAGGAGQGGY GGLGSQGTSGRGGLGGQ-GAGAAAAAGGAGQGGYGGLGSQGTSGRG-GLGGQGAGAAA AAGGAGQGGYGGLGSQGTSGRG-GLGGQGAGAAAAAGGAGQGGYGGLGSQGTSGRG GLGGQGAGAAAAAGGAGQGGYGGLG-SQGTSGRGGLGGQGAGAAAAAGGAGQGGYG GLG-SQGTSGRGGLGGQGAGAAAAAGGAGQG-GYGGLGSQGTSGRGGLGGQGAGAAAA AGGAGQGGYGGLGSQGTSGRGGLGGQ-GAGAAAAAGGAGQGGYGGLGSQGTSGRGGL GGQ-GAGAAAAAGGAGQGGYGGLGSQGTSGRG-GLGGQGAGAAAAAGGAGQGGYGGL GSQGTSGRGGLGGQGAGAAAAAGGAGQG-GYGGLGSQGTSGRGGLGGQGAGAAAAA GGAGQG-GYGGLGSQGTSRGDCGSESEFPVQSSS-DSSEENGNGDSSEEEEEEEENSNEEE NNEENEDSDGNEDKLHHHHHH (SEQ ID NO: 12)

One of two complementary oligonucleotide sequences for the linker carrying the SpeI site flanked by sequences encoding the amino acids CRGD (SEQ ID NO: 2) to obtain pET30-linkGGATCCTGTCGCGGTGACACTAGTCGCGGTGAC TGTG (SEQ ID NO: 13)

One of two complementary oligonucleotide sequences for the linker carrying the SpeI site flanked by sequences encoding the amino acids CRGD (SEQ ID NO: 2) to obtain pET30-link GGATCCACAGTCACCGCGACTAGTGTCACC GCG ACAG (SEQ ID NO: 14)

One of two complementary oligonucleotide sequences for the R5 peptide (contains the 19 amino-acid R5 peptide of the Sil1 protein) which were designed with EcoRI and NotI sites at the 5' and 3' ends respectively (SEQ ID NO: 15)

```
5' aattcagcagcaaaaaaagcggcagctattcgggcagcaaaggcag caaacgccgcatcctcgc 3'
```

One of two complementary oligonucleotide sequences for the R5 peptide (contains the 19 amino-acid R5 peptide of the Sil1 protein) which were designed with EcoRI and NotI sites at the 5' and 3' ends respectively.

(SEQ ID NO: 16)

```
3' gtcgtcgtttttttcgccgtcgataagcccgtcgtttccgtcgttt gcggcgtaggagcgccgg 5'
```

The amino acid sequence of the R5 peptide of Sil1 protein from *C. fusiformis* is:

SSKKSGSYSGSKGSKRRIL (SEQ ID NO: 17)

The amino acid sequence of the R2 peptide of Sil1 protein from *C. fusiformis* is:

SSKKSGSYSGYSTKKSGSRRIL, (SEQ ID NO: 18)

The amino acid sequence of the R3 peptide of Sil1 protein from *C. fusiformis* is:

SSKKSGSYSGYSKGSKRRIL, (SEQ ID NO: 19)

The amino acid sequence of the R4/R6 peptide of Sil1 protein from *C. fusiformis* is:

SSKKSGSYSGYSKGSKRRNL. (SEQ ID NO: 20)

The amino acid sequence of the R1 peptide of Sil1 protein from *C. fusiformis* is:

SSKKSGSYYSYGTKK. (SEQ ID NO: 21)

Bone Sialoprotein Precursor [*Homo sapiens*] Accession AAC95490 is:

(SEQ ID NO: 22)

```
MKTALILLSI LGMACAFSMK NLHRRVKIED SEENGVFKYR

PRYYLYKHAY FYPHLKRFPV QGSSDSSEEN GDDSSEEEEE

EEETSNEGEN NEESNEDEDS EAENTTLSAT TLGYGEDATP

GTGYTGLAAI QLPKKAGDIT NKATKEKESD EEEEEEEEGN

ENEESEAEVD ENEQGINGTS TNSTEAENGN GSSGGDNGEE

GEEESVTGAN AEGTTETGGQ GKGTSKTTTS PNGGFEPTTP

PQVYRTTSPP FGKTTTVEYE GEYEYTGVNE YDNGYEIYES

ENGEPRGDNY RAYEDEYSYF KGQGYDGYDG QNYYHHQ
```

Silaffin 1 precursor (natSil-1) [Contains: Silaffin-1B; Silaffin-1A2; Silaffin-1A1] Accession Q9SE35: MKLTAIFPLL FTAVGYCAAQ SIADLAAANL STEDSKSAQL ISADSS-DDAS DSSVESVDAA SSDVSGSSVE SVDVSGSSLE SVDVSGSSLE SVDDSSEDSE EEELRILSSK KSG-SYYSYGT KKSGSYSGYS TKKSASRRIL SSKKSG-SYSG YSTKKSGSRR ILSSKKSGSY SGSKGSKRRI LSSKKSGSYS GSKGSKRRNL SSKKSGSYSG SKG-SKRRILS SKKSGSYSGS KGSKRRNLSS KKSG-SYSGSK GSKRRILSGG LRGSM (SEQ ID NO: 23)

CRGD15mer-R5: Sequence of fusion protein; fusion of CRGD15mer to the amino acid sequence of the R5 peptide of Sil1 protein from *C. fusiformis*. MASMTGGQQM GRG-SCRGDTS GRGGLGGQGA GAAAAAGGAG QGGYG-GLGSQ GTSGRGGLGG QGAGAAAAAG GAGQG-GYGGL GSQGTSGRGG LGGQGAGAAA AAGGAGQGGY GGLGSQGTSG RGGLGGQGAG AAAAAGGAGQ GGYGGLGSQG TSGRGGLGGQ GAGAAAAAGG AGQGGYGGLG SQGTSGRGGL GGQ-GAGAAAA AGGAGQGGYG GLGSQGTSGR GGLGGQ-GAGA AAAAGGAGQG GYGGLGSQGT SGRGGLG-GQG AGAAAAAGGA GQGGYGGLGS QGTSGRGGLG GQGAGAAAAA GGAGQGGYGG LGSQGTSGRG GLG-GQGAGAA AAAGGAGQGG YGGLGSQGTS GRGGLG-GQGA GAAAAAGGAG QGGYGGLGSQ GTSGRG-GLGG QGAGAAAAAG GAGQGGYGGL GSQGTSGRGG LGGQGAGAAA AAGGAGQGGY GGLGSQGTSG RGGLGGQGAG AAAAAGGAGQ GGYGGLGSQG TSGRGGLGGQ GAGAAAAAGG AGQGGYGGLG SQGTSRGDCG SEFSSKKSGS YSG-SKGSKRR ILCGRHHHHH H (SEQ ID NO: 24)

15mer-R5: Sequence of fusion protein; fusion of 15mer to the amino acid sequence of the R5 peptide of Sil1 protein from *C. fusiformis*. MHHHHHHSSG LVPRGSGMKE TAAAKFERQH MDSPDLGTDD DDKAMASGRG GLG-GQGAGAA AAAGGAGQGG YGGLGSQGTS GRGGLG-GQGA GAAAAAGGAG QGGYGGLGSQ GTSGRG-GLGG QGAGAAAAAG GAGQGGYGGL GSQGTSGRGG LGGQGAGAAA AAGGAGQGGY GGLGSQGTSG RGGLGGQGAG AAAAAGGAGQ GGYGGLGSQG TSGRGGLGGQ GAGAAAAAGG AGQGGYGGLG SQGTSGRGGL GGQGAGAAAA AGGAGQGGYG GLGSQGTSGR GGLGGQGAGA AAAAGGAGQG GYGGLGSQGT SGRGGLGGQG AGAAAAAGGA GQGGYGGLGS QGTSGRGGLG GQGAGAAAAA GGAGQGGYGG LGSQGTSGRG GLG-GQGAGAA AAAGGAGQGG YGGLGSQGTS GRGGLG-GQGA GAAAAAGGAG QGGYGGLGSQ GTSGRG-GLGG QGAGAAAAAG GAGQGGYGGL GSQGTSGRGG LGGQGAGAAA AAGGAGQGGY GGLGSQGTSG RGGLGGQGAG AAAAAGGAGQ GGYGGLGSQG TSSSKKSGSY SGSKGSKRRIL (SEQ ID NO: 25)

PCR PRIMER BamH I site, C-DMP1f: 5'-CA GGATCCAGGGGTGACAACCCAGAT-3' (SEQ ID NO: 26)

PCR PRIMER Xho I site, C-DMP1r: 5' GCC TCGAGGTAGCCATCTTGGCAATC-3' (SEQ ID NO: 27).

The references cited herein and throughout the application are incorporated by reference.

REFERENCES

1. Kroger, N., Deutzmann, R. & Sumper, M. (1999). Polycationic peptides from diatom biosilica that direct silica nanosphere formation. Science 286, 1129-32.
2. Kroger, N., Deutzmann, R. & Sumper, M. (2001). Silica-precipitating peptides from diatoms. The chemical structure of silaffin-A from *Cylindrotheca fusiformis*. J Biol Chem 276, 26066-70.
3. Kroger, N., Deutzmann, R., Bergsdorf, C. & Sumper, M. (2000). Species-specific polyamines from diatoms control silica morphology. Proc Natl Acad Sci USA 97, 14133-8.

4. Kroger, N., Lorenz, S., Brunner, E. & Sumper, M. (2002). Self-assembly of highly phosphorylated silaffins and their function in biosilica morphogenesis. Science 298, 584-6.
5. Poulsen, N., Sumper, M. & Kroger, N. (2003). Biosilica formation in diatoms: characterization of native silaffin-2 and its role in silica morphogenesis. Proc Natl Acad Sci USA 100, 12075-80.
6. Rodriguez, F., Glawe, D. D., Naik, R. R., Hallinan, K. P. & Stone, M. O. (2004). Study of the chemical and physical influences upon in vitro peptide-mediated silica formation. Biomacromolecules 5, 261-5.
7. Naik, R. R., Whitlock, P. W., Rodriguez, F., Brott, L. L., Glawe, D. D., Clarson, S. J. & Stone, M. O. (2003). Controlled formation of biosilica structures in vitro. Chem Commun (Camb), 238-9.
8. Patwardhan, S. V. & Clarson, S. J. (2002). Silicification and biosilicification. Part 4. Effect of template size on the formation of silica. Journal of Inorganic and Organometallic Polymers 12, 109-116.
9. Patwardhan, S. V. & Clarson, S. J. (2003). Silicification and biosilicification: Part 5. An investigation of the silica structures formed at weakly acidic pH and neutral pH as facilitated by cationically charged macromolecules. Materials Science and Engineering C 23, 495-499.
10. Prince, J. T., McGrath, K. P., DiGirolamo, C. M. & Kaplan, D. L. (1995). Construction, cloning, and expression of synthetic genes encoding spider dragline silk. Biochemistry 34, 10879-85.
11. Winkler, S., Wilson, D. & Kaplan, D. L. (2000). Controlling beta-sheet assembly in genetically engineered silk by enzymatic Phosphorylation/Dephosphorylation, by. Biochemistry 39, 14002.
12. Yan, S. Z., Beeler, J. A., Chen, Y., Shelton, R. K. & Tang, W. J. (2001). The regulation of type 7 adenylyl cyclase by its C1b region and *Escherichia coli* peptidylprolyl isomerase, SlyD. J Biol Chem 276, 8500-6.
13. Huang, J., Valluzzi, R., Bini, E., Vernaglia, B. & Kaplan, D. L. (2003). Cloning, expression, and assembly of sericin-like protein. J Biol Chem 278, 46117-23.
14. Sumper, M. & Kroger, N. (2004). Silica formation in diatoms: the function of long-chain polyamines and silaffins. J Mater Chem 14, 2059-2065.
15. Jin, H. J., Fridrikh, S. V., Rutledge, G. C. & Kaplan, D. L. (2002). Electrospinning *Bombyx mori* silk with poly(ethylene oxide). Biomacromolecules 3, 1233-1239.

What is claimed is:

1. A method for forming a fibrous protein inorganic-composite comprising:
   (a) contacting a fusion protein with an inorganic material capable of mineralizing for a sufficient period of time to allow mineralization of the inorganic material, wherein the fusion protein comprises a fibrous protein domain and a mineralizing domain, wherein the fibrous protein domain is obtained from silk and comprises a repeat unit as set forth in SEQ ID NO: 1, and wherein the mineralizing domain is capable of inducing mineralization and wherein the mineralizing domain is obtained from dentin matrix protein 1 (DMP1).

2. The method of claim 1, wherein the fibrous protein domain is from the silk protein Spidroin 1.

3. The method of claim 1, wherein the mineralizing domain induces the formation of hydroxyapatite, silica, cadmium sulfide or magnetite.

4. The method of claim 1, wherein the mineralization domain is obtained from dentin matrix protein 1 (DMP1).

5. The method of claim 4, wherein the mineralization domain is derived from dentin matrix protein 1 (DMP1) and comprises the amino acid sequence of SEQ ID NO: 6 or SEQ ID NO: 7.

6. The method of claim 1, wherein the fusion protein comprises an amino acid sequence selected from the group consisting of SEQ ID NO: 9, and SEQ ID NO: 10.

7. The method of claim 1, wherein the inorganic material forms hydroxyapatite or silica.

8. The method of claim 1, wherein the fusion protein comprises a fiber, a film, or a sponge.

9. The method of claim 8, wherein the fiber, film, or sponge further comprises an agent.

10. The method of claim 9, wherein the agent is selected from the group consisting of a protein, peptide, nucleic acid, PNA, aptamer, antibody and a small molecule.

* * * * *

```
                         SEQUENCE LISTING

<160> NUMBER OF SEQ ID NOS: 27

<210> SEQ ID NO 1
<211> LENGTH: 33
<212> TYPE: PRT
<213> ORGANISM: Nephila clavipes

<400> SEQUENCE: 1

Ser Gly Arg Gly Gly Leu Gly Gly Gln Gly Ala Gly Ala Ala Ala
1               5                   10                  15

Ala Gly Gly Ala Gly Gln Gly Gly Tyr Gly Gly Leu Gly Ser Gln Gly
            20                  25                  30

Thr

<210> SEQ ID NO 2
<211> LENGTH: 4
<212> TYPE: PRT
<213> ORGANISM: Artificial Sequence
<220> FEATURE:
<223> OTHER INFORMATION: Description of Artificial Sequence: Synthetic
      linker peptide

<400> SEQUENCE: 2

Cys Arg Gly Asp
1

<210> SEQ ID NO 3
<211> LENGTH: 38
<212> TYPE: PRT
<213> ORGANISM: Nephila clavipes

<400> SEQUENCE: 3

Cys Arg Gly Asp Thr Ser Gly Arg Gly Gly Leu Gly Gly Gln Gly Ala
1               5                   10                  15

Gly Ala Ala Ala Ala Gly Gly Ala Gly Gln Gly Gly Tyr Gly Gly
            20                  25                  30

Leu Gly Ser Gln Gly Thr
        35
```

<210> SEQ ID NO 4
<211> LENGTH: 518
<212> TYPE: PRT
<213> ORGANISM: Nephila clavipes

<400> SEQUENCE: 4

Met Ala Ser Met Thr Gly Gly Gln Gln Met Gly Arg Gly Ser Ala Met
1               5                   10                  15

Ala Ser Gly Arg Gly Gly Leu Gly Gly Gln Gly Ala Gly Ala Ala Ala
            20                  25                  30

Ala Ala Gly Gly Ala Gly Gln Gly Gly Tyr Gly Gly Leu Gly Ser Gln
        35                  40                  45

Gly Thr Ser Gly Arg Gly Gly Leu Gly Gly Gln Gly Ala Gly Ala Ala
    50                  55                  60

Ala Ala Ala Gly Gly Ala Gly Gln Gly Gly Tyr Gly Gly Leu Gly Ser
65                  70                  75                  80

Gln Gly Thr Ser Gly Arg Gly Gly Leu Gly Gly Gln Gly Ala Gly Ala
                85                  90                  95

Ala Ala Ala Ala Gly Gly Ala Gly Gln Gly Gly Tyr Gly Gly Leu Gly
            100                 105                 110

Ser Gln Gly Thr Ser Gly Arg Gly Gly Leu Gly Gly Gln Gly Ala Gly
        115                 120                 125

Ala Ala Ala Ala Gly Gly Ala Gly Gln Gly Gly Tyr Gly Gly Leu
    130                 135                 140

Gly Ser Gln Gly Thr Ser Gly Arg Gly Gly Leu Gly Gly Gln Gly Ala
145                 150                 155                 160

Gly Ala Ala Ala Ala Gly Gly Ala Gly Gln Gly Gly Tyr Gly Gly
                165                 170                 175

Leu Gly Ser Gln Gly Thr Ser Gly Arg Gly Gly Leu Gly Gly Gln Gly
            180                 185                 190

Ala Gly Ala Ala Ala Ala Gly Gly Ala Gly Gln Gly Gly Tyr Gly
        195                 200                 205

Gly Leu Gly Ser Gln Gly Thr Ser Gly Arg Gly Gly Leu Gly Gly Gln
    210                 215                 220

Gly Ala Gly Ala Ala Ala Ala Gly Gly Ala Gly Gln Gly Gly Tyr
225                 230                 235                 240

Gly Gly Leu Gly Ser Gln Gly Thr Ser Gly Arg Gly Gly Leu Gly Gly
                245                 250                 255

Gln Gly Ala Gly Ala Ala Ala Ala Gly Gly Ala Gly Gln Gly Gly
            260                 265                 270

Tyr Gly Gly Leu Gly Ser Gln Gly Thr Ser Gly Arg Gly Gly Leu Gly
        275                 280                 285

Gly Gln Gly Ala Gly Ala Ala Ala Ala Gly Gly Ala Gly Gln Gly
    290                 295                 300

Gly Tyr Gly Gly Leu Gly Ser Gln Gly Thr Ser Gly Arg Gly Gly Leu
305                 310                 315                 320

Gly Gly Gln Gly Ala Gly Ala Ala Ala Ala Gly Gly Ala Gly Gln
                325                 330                 335

Gly Gly Tyr Gly Gly Leu Gly Ser Gln Gly Thr Ser Gly Arg Gly Gly
            340                 345                 350

Leu Gly Gly Gln Gly Ala Gly Ala Ala Ala Ala Gly Gly Ala Gly
        355                 360                 365

Gln Gly Gly Tyr Gly Gly Leu Gly Ser Gln Gly Thr Ser Gly Arg Gly
    370                 375                 380

```
Gly Leu Gly Gly Gln Gly Ala Gly Ala Ala Ala Ala Gly Gly Ala
385                 390                 395                 400

Gly Gln Gly Gly Tyr Gly Gly Leu Gly Ser Gln Gly Thr Ser Gly Arg
            405                 410                 415

Gly Gly Leu Gly Gly Gln Gly Ala Gly Ala Ala Ala Ala Gly Gly
            420                 425                 430

Ala Gly Gln Gly Gly Tyr Gly Gly Leu Gly Ser Gln Gly Thr Ser Gly
            435                 440                 445

Arg Gly Gly Leu Gly Gly Gln Gly Ala Gly Ala Ala Ala Ala Gly
            450                 455                 460

Gly Ala Gly Gln Gly Gly Tyr Gly Gly Leu Gly Ser Gln Gly Thr Ser
465                 470                 475                 480

Gly Arg Gly Gly Leu Gly Gly Gln Gly Ala Gly Ala Ala Ala Ala
            485                 490                 495

Gly Gly Ala Gly Gln Gly Gly Tyr Gly Gly Leu Gly Ser Gln Gly Thr
                500                 505                 510

Ser His His His His His
            515
```

<210> SEQ ID NO 5
<211> LENGTH: 527
<212> TYPE: PRT
<213> ORGANISM: Nephila clavipes

<400> SEQUENCE: 5

```
Met Ala Ser Met Thr Gly Gly Gln Gln Met Gly Arg Gly Ser Cys Arg
1               5                   10                  15

Gly Asp Thr Ser Gly Arg Gly Gly Leu Gly Gly Gln Gly Ala Gly Ala
            20                  25                  30

Ala Ala Ala Ala Gly Gly Ala Gly Gln Gly Gly Tyr Gly Gly Leu Gly
        35                  40                  45

Ser Gln Gly Thr Ser Gly Arg Gly Gly Leu Gly Gly Gln Gly Ala Gly
    50                  55                  60

Ala Ala Ala Ala Ala Gly Gly Ala Gly Gln Gly Gly Tyr Gly Gly Leu
65                  70                  75                  80

Gly Ser Gln Gly Thr Ser Gly Arg Gly Gly Leu Gly Gly Gln Gly Ala
            85                  90                  95

Gly Ala Ala Ala Ala Gly Gly Ala Gly Gln Gly Gly Tyr Gly Gly
            100                 105                 110

Leu Gly Ser Gln Gly Thr Ser Gly Arg Gly Gly Leu Gly Gly Gln Gly
        115                 120                 125

Ala Gly Ala Ala Ala Ala Gly Gly Ala Gly Gln Gly Gly Tyr Gly
    130                 135                 140

Gly Leu Gly Ser Gln Gly Thr Ser Gly Arg Gly Gly Leu Gly Gly Gln
145                 150                 155                 160

Gly Ala Gly Ala Ala Ala Ala Gly Gly Ala Gly Gln Gly Gly Tyr
            165                 170                 175

Gly Gly Leu Gly Ser Gln Gly Thr Ser Gly Arg Gly Gly Leu Gly Gly
        180                 185                 190

Gln Gly Ala Gly Ala Ala Ala Ala Gly Gly Ala Gly Gln Gly Gly
    195                 200                 205

Tyr Gly Gly Leu Gly Ser Gln Gly Thr Ser Gly Arg Gly Gly Leu Gly
    210                 215                 220

Gly Gln Gly Ala Gly Ala Ala Ala Ala Ala Gly Gly Ala Gly Gln Gly
225                 230                 235                 240
```

-continued

```
Gly Tyr Gly Gly Leu Gly Ser Gln Gly Thr Ser Gly Arg Gly Gly Leu
            245                 250                 255
Gly Gly Gln Gly Ala Gly Ala Ala Ala Ala Gly Gly Ala Gly Gln
        260                 265                 270
Gly Gly Tyr Gly Gly Leu Gly Ser Gln Gly Thr Ser Gly Arg Gly Gly
        275                 280                 285
Leu Gly Gly Gln Gly Ala Gly Ala Ala Ala Ala Gly Gly Ala Gly
        290                 295                 300
Gln Gly Gly Tyr Gly Gly Leu Gly Ser Gln Gly Thr Ser Gly Arg Gly
305                 310                 315                 320
Gly Leu Gly Gly Gln Gly Ala Gly Ala Ala Ala Ala Gly Gly Ala
            325                 330                 335
Gly Gln Gly Gly Tyr Gly Gly Leu Gly Ser Gln Gly Thr Ser Gly Arg
            340                 345                 350
Gly Gly Leu Gly Gly Gln Gly Ala Gly Ala Ala Ala Ala Gly Gly
            355                 360                 365
Ala Gly Gln Gly Gly Tyr Gly Gly Leu Gly Ser Gln Gly Thr Ser Gly
            370                 375                 380
Arg Gly Gly Leu Gly Gly Gln Gly Ala Gly Ala Ala Ala Ala Gly
385                 390                 395                 400
Gly Ala Gly Gln Gly Gly Tyr Gly Gly Leu Gly Ser Gln Gly Thr Ser
                405                 410                 415
Gly Arg Gly Gly Leu Gly Gly Gln Gly Ala Gly Ala Ala Ala Ala
                420                 425                 430
Gly Gly Ala Gly Gln Gly Gly Tyr Gly Gly Leu Gly Ser Gln Gly Thr
            435                 440                 445
Ser Gly Arg Gly Gly Leu Gly Gly Gln Gly Ala Gly Ala Ala Ala Ala
450                 455                 460
Ala Gly Gly Ala Gly Gln Gly Gly Tyr Gly Gly Leu Gly Ser Gln Gly
465                 470                 475                 480
Thr Ser Gly Arg Gly Gly Leu Gly Gly Gln Gly Ala Gly Ala Ala Ala
                485                 490                 495
Ala Ala Gly Gly Ala Gly Gln Gly Gly Tyr Gly Gly Leu Gly Ser Gln
            500                 505                 510
Gly Thr Ser Arg Gly Asp Cys Gly Ser His His His His His His
            515                 520                 525
```

<210> SEQ ID NO 6
<211> LENGTH: 156
<212> TYPE: PRT
<213> ORGANISM: Rattus norvegicus

<400> SEQUENCE: 6

```
Arg Gly Asp Asn Pro Asp Asn Thr Ser Gln Thr Gly Asp Gln Arg Asp
1               5                   10                  15
Ser Glu Ser Ser Glu Glu Asp Arg Leu Asn Thr Phe Ser Ser Ser Glu
            20                  25                  30
Ser Gln Ser Thr Glu Glu Gln Gly Asp Ser Glu Ser Asn Glu Ser Leu
        35                  40                  45
Ser Leu Ser Glu Glu Ser Gln Glu Ser Ala Gln Asp Glu Asp Ser Ser
    50                  55                  60
Ser Gln Glu Gly Leu Gln Ser Gln Ser Ala Ser Arg Glu Ser Arg Ser
65                  70                  75                  80
Gln Glu Ser Gln Ser Glu Glu Asp Ser Arg Ser Glu Glu Asn Arg Asp
                85                  90                  95
```

-continued

Ser Asp Ser Gln Asp Ser Ser Arg Ser Lys Glu Glu Ser Asn Ser Thr
            100                 105                 110

Gly Ser Thr Ser Ser Glu Glu Asp Asn His Pro Lys Asn Ile Glu
        115                 120                 125

Ala Asp Asn Arg Lys Leu Ile Val Asp Ala Tyr His Asn Lys Pro Ile
130                 135                 140

Gly Asp Gln Asp Asp Asn Asp Cys Gln Asp Gly Tyr
145                 150                 155

<210> SEQ ID NO 7
<211> LENGTH: 473
<212> TYPE: PRT
<213> ORGANISM: Rattus norvegicus

<400> SEQUENCE: 7

Leu Pro Val Ala Arg Tyr Gln Asn Thr Glu Ser Glu Ser Ser Glu Glu
1               5                   10                  15

Arg Thr Gly Asn Leu Ala Gln Ser Pro Pro Pro Met Ala Asn Ser
            20                  25                  30

Asp His Thr Asp Ser Ser Glu Ser Gly Glu Glu Leu Gly Ser Asp Arg
            35                  40                  45

Ser Gln Tyr Arg Pro Ala Gly Gly Leu Ser Lys Ser Ala Gly Met Asp
50                  55                  60

Ala Asp Lys Glu Glu Asp Glu Asp Ser Gly Asp Asp Thr Phe Gly
65                  70                  75                  80

Asp Glu Asp Asn Gly Pro Gly Pro Glu Glu Arg Gln Trp Gly Gly Pro
                85                  90                  95

Ser Arg Leu Asp Ser Asp Glu Asp Ser Ala Asp Thr Thr Gln Ser Ser
            100                 105                 110

Glu Asp Ser Thr Ser Gln Glu Asn Ser Ala Gln Asp Thr Pro Ser Asp
            115                 120                 125

Ser Lys Asp His His Ser Asp Glu Ala Asp Ser Arg Pro Glu Ala Gly
            130                 135                 140

Asp Ser Thr Gln Asp Ser Glu Ser Glu Tyr Arg Val Gly Gly Gly
145                 150                 155                 160

Ser Glu Gly Glu Ser Ser His Gly Asp Gly Ser Glu Phe Asp Asp Glu
                165                 170                 175

Gly Met Gln Ser Asp Asp Pro Gly Ser Thr Arg Ser Asp Arg Gly His
            180                 185                 190

Thr Arg Met Ser Ser Ala Asp Ile Ser Ser Glu Glu Ser Lys Gly Asp
            195                 200                 205

His Glu Pro Thr Ser Thr Gln Asp Ser Asp Asp Ser Gln Asp Val Glu
210                 215                 220

Phe Ser Ser Arg Lys Ser Phe Arg Arg Ser Arg Val Ser Glu Glu Asp
225                 230                 235                 240

Asp Arg Gly Glu Leu Ala Asp Ser Asn Ser Arg Glu Thr Gln Ser Val
                245                 250                 255

Ser Thr Glu Asp Phe Arg Ser Lys Glu Glu Ser Arg Ser Glu Thr Gln
            260                 265                 270

Glu Asp Thr Ala Glu Thr Gln Ser Gln Glu Asp Ser Pro Glu Gly Gln
            275                 280                 285

Asp Pro Ser Ser Glu Ser Ser Glu Glu Ala Gly Glu Pro Ser Gln Glu
            290                 295                 300

Ser Ser Ser Glu Ser Gln Glu Gly Val Ala Ser Glu Ser Arg Gly Asp
305                 310                 315                 320

```
Asn Pro Asp Asn Thr Ser Gln Thr Gly Asp Gln Arg Asp Ser Glu Ser
                325                 330                 335

Ser Glu Glu Asp Arg Leu Asn Thr Phe Ser Ser Glu Ser Gln Ser
            340                 345                 350

Thr Glu Glu Gln Gly Asp Ser Glu Ser Asn Glu Ser Leu Ser Leu Ser
        355                 360                 365

Glu Glu Ser Gln Glu Ser Ala Gln Asp Glu Asp Ser Ser Ser Gln Glu
    370                 375                 380

Gly Leu Gln Ser Gln Ser Ala Ser Arg Glu Ser Arg Ser Gln Glu Ser
385                 390                 395                 400

Gln Ser Glu Glu Asp Ser Arg Ser Glu Glu Asn Arg Asp Ser Asp Ser
            405                 410                 415

Gln Asp Ser Ser Arg Ser Lys Glu Glu Ser Asn Ser Thr Gly Ser Thr
        420                 425                 430

Ser Ser Ser Glu Glu Asp Asn His Pro Lys Asn Ile Glu Ala Asp Asn
    435                 440                 445

Arg Lys Leu Ile Val Asp Ala Tyr His Asn Lys Pro Ile Gly Asp Gln
450                 455                 460

Asp Asp Asn Asp Cys Gln Asp Gly Tyr
465                 470

<210> SEQ ID NO 8
<211> LENGTH: 48
<212> TYPE: PRT
<213> ORGANISM: Unknown
<220> FEATURE:
<223> OTHER INFORMATION: Description of Unknown: Unknown bone
      sialoprotein sequence of mammal origin

<400> SEQUENCE: 8

Ser Glu Phe Pro Val Gln Ser Ser Asp Ser Ser Glu Glu Asn Gly
1               5                   10                  15

Asn Gly Asp Ser Ser Glu Glu Glu Glu Glu Glu Glu Asn Ser Asn
            20                  25                  30

Glu Glu Glu Asn Asn Glu Glu Asn Glu Asp Ser Asp Gly Asn Glu Asp
        35                  40                  45

<210> SEQ ID NO 9
<211> LENGTH: 675
<212> TYPE: PRT
<213> ORGANISM: Artificial Sequence
<220> FEATURE:
<223> OTHER INFORMATION: Description of Artificial Sequence: Synthetic
      fusion protein

<400> SEQUENCE: 9

Met Ala Ser Met Thr Gly Gly Gln Gln Met Gly Arg Cys Arg Gly Asp
1               5                   10                  15

Thr Ser Gly Arg Gly Gly Leu Gly Gly Gln Ala Gly Ala Ala
            20                  25                  30

Ala Ala Gly Gly Ala Gly Gln Gly Gly Tyr Gly Gly Leu Gly Ser Gln
        35                  40                  45

Gly Thr Ser Gly Arg Gly Gly Leu Gly Gly Gln Gly Ala Gly Ala Ala
    50                  55                  60

Ala Ala Ala Gly Gly Ala Gly Gln Gly Gly Tyr Gly Gly Leu Gly Ser
65                  70                  75                  80

Gln Gly Thr Ser Gly Arg Gly Gly Leu Gly Gly Gln Gly Ala Gly Ala
                85                  90                  95

Ala Ala Ala Ala Gly Gly Ala Gly Gln Gly Gly Tyr Gly Gly Leu Gly
```

```
                100                 105                 110
Ser Gln Gly Thr Ser Gly Arg Gly Gly Leu Gly Gly Gln Gly Ala Gly
            115                 120                 125

Ala Ala Ala Ala Ala Gly Gly Ala Gly Gln Gly Gly Tyr Gly Gly Leu
        130                 135                 140

Gly Ser Gln Gly Thr Ser Gly Arg Gly Gly Leu Gly Gly Gln Gly Ala
145                 150                 155                 160

Gly Ala Ala Ala Ala Ala Gly Gly Ala Gly Gln Gly Gly Tyr Gly Gly
                165                 170                 175

Leu Gly Ser Gln Gly Thr Ser Gly Arg Gly Gly Leu Gly Gly Gln Gly
            180                 185                 190

Ala Gly Ala Ala Ala Ala Gly Gly Ala Gly Gln Gly Gly Tyr Gly
        195                 200                 205

Gly Leu Gly Ser Gln Gly Thr Ser Gly Arg Gly Gly Leu Gly Gly Gln
    210                 215                 220

Gly Ala Gly Ala Ala Ala Ala Gly Gly Ala Gly Gln Gly Gly Tyr
225                 230                 235                 240

Gly Gly Leu Gly Ser Gln Gly Thr Ser Gly Arg Gly Gly Leu Gly Gly
                245                 250                 255

Gln Gly Ala Gly Ala Ala Ala Ala Gly Gly Ala Gly Gln Gly Gly
            260                 265                 270

Tyr Gly Gly Leu Gly Ser Gln Gly Thr Ser Gly Arg Gly Gly Leu Gly
        275                 280                 285

Gly Gln Gly Ala Gly Ala Ala Ala Ala Gly Gly Ala Gly Gln Gly
    290                 295                 300

Gly Tyr Gly Gly Leu Gly Ser Gln Gly Thr Ser Gly Arg Gly Gly Leu
305                 310                 315                 320

Gly Gly Gln Gly Ala Gly Ala Ala Ala Ala Gly Gly Ala Gly Gln
                325                 330                 335

Gly Gly Tyr Gly Gly Leu Gly Ser Gln Gly Thr Ser Gly Arg Gly Gly
            340                 345                 350

Leu Gly Gly Gln Gly Ala Gly Ala Ala Ala Ala Gly Gly Ala Gly
        355                 360                 365

Gln Gly Gly Tyr Gly Gly Leu Gly Ser Gln Gly Thr Ser Gly Arg Gly
    370                 375                 380

Gly Leu Gly Gly Gln Gly Ala Gly Ala Ala Ala Ala Gly Gly Ala
385                 390                 395                 400

Gly Gln Gly Gly Tyr Gly Gly Leu Gly Ser Gln Gly Thr Ser Gly Arg
                405                 410                 415

Gly Gly Leu Gly Gly Gln Gly Ala Gly Ala Ala Ala Ala Gly Gly
            420                 425                 430

Ala Gly Gln Gly Gly Tyr Gly Gly Leu Gly Ser Gln Gly Thr Ser Gly
        435                 440                 445

Arg Gly Gly Leu Gly Gly Gln Gly Ala Gly Ala Ala Ala Ala Gly
    450                 455                 460

Gly Ala Gly Gln Gly Gly Tyr Gly Gly Leu Gly Ser Gln Gly Thr Ser
465                 470                 475                 480

Gly Arg Gly Gly Leu Gly Gly Gln Gly Ala Gly Ala Ala Ala Ala
                485                 490                 495

Gly Gly Ala Gly Gln Gly Gly Tyr Gly Gly Leu Gly Ser Gln Gly Thr
            500                 505                 510

Ser Arg Gly Asp Cys Gly Ser Arg Gly Asp Asn Pro Asp Asn Thr Ser
        515                 520                 525
```

```
Gln Thr Gly Asp Gln Arg Asp Ser Glu Ser Ser Glu Glu Asp Arg Leu
            530                 535                 540

Asn Thr Phe Ser Ser Ser Glu Ser Gln Ser Thr Glu Glu Gln Gly Asp
545                 550                 555                 560

Ser Glu Ser Asn Glu Ser Leu Ser Leu Ser Glu Glu Ser Gln Glu Ser
                565                 570                 575

Ala Gln Asp Glu Asp Ser Ser Ser Gln Glu Gly Leu Gln Ser Gln Ser
            580                 585                 590

Ala Ser Arg Glu Ser Arg Ser Gln Glu Ser Gln Ser Glu Glu Asp Ser
        595                 600                 605

Arg Ser Glu Glu Asn Arg Asp Ser Asp Ser Gln Asp Ser Ser Arg Ser
        610                 615                 620

Lys Glu Glu Ser Asn Ser Thr Gly Ser Thr Ser Ser Ser Glu Glu Asp
625                 630                 635                 640

Asn His Pro Lys Asn Ile Glu Ala Asp Asn Arg Lys Leu Ile Val Asp
                645                 650                 655

Ala Tyr His Asn Lys Pro Ile Gly Asp Gln Asp Asp Asn Asp Cys Gln
            660                 665                 670

Asp Gly Tyr
        675

<210> SEQ ID NO 10
<211> LENGTH: 992
<212> TYPE: PRT
<213> ORGANISM: Artificial Sequence
<220> FEATURE:
<223> OTHER INFORMATION: Description of Artificial Sequence: Synthetic
      fusion protein

<400> SEQUENCE: 10

Met Ala Ser Met Thr Gly Gly Gln Gln Met Gly Arg Cys Arg Gly Asp
1               5                   10                  15

Thr Ser Gly Arg Gly Gly Leu Gly Gly Gln Gly Ala Gly Ala Ala Ala
            20                  25                  30

Ala Ala Gly Gly Ala Gly Gln Gly Gly Tyr Gly Gly Leu Gly Ser Gln
        35                  40                  45

Gly Thr Ser Gly Arg Gly Gly Leu Gly Gly Gln Gly Ala Gly Ala Ala
    50                  55                  60

Ala Ala Ala Gly Gly Ala Gly Gln Gly Gly Tyr Gly Gly Leu Gly Ser
65                  70                  75                  80

Gln Gly Thr Ser Gly Arg Gly Gly Leu Gly Gly Gln Gly Ala Gly Ala
                85                  90                  95

Ala Ala Ala Gly Gly Ala Gly Gln Gly Gly Tyr Gly Gly Leu Gly
            100                 105                 110

Ser Gln Gly Thr Ser Gly Arg Gly Gly Leu Gly Gly Gln Gly Ala Gly
        115                 120                 125

Ala Ala Ala Ala Gly Gly Ala Gly Gln Gly Gly Tyr Gly Gly Leu
    130                 135                 140

Gly Ser Gln Gly Thr Ser Gly Arg Gly Gly Leu Gly Gly Gln Gly Ala
145                 150                 155                 160

Gly Ala Ala Ala Ala Gly Gly Ala Gly Gln Gly Gly Tyr Gly Gly
                165                 170                 175

Leu Gly Ser Gln Gly Thr Ser Gly Arg Gly Gly Leu Gly Gly Gln Gly
            180                 185                 190

Ala Gly Ala Ala Ala Ala Gly Gly Ala Gly Gln Gly Gly Tyr Gly
        195                 200                 205
```

```
Gly Leu Gly Ser Gln Gly Thr Ser Gly Arg Gly Gly Leu Gly Gly Gln
            210                 215                 220
Gly Ala Gly Ala Ala Ala Ala Gly Gly Ala Gly Gln Gly Gly Tyr
225                 230                 235                 240
Gly Gly Leu Gly Ser Gln Gly Thr Ser Gly Arg Gly Gly Leu Gly Gly
            245                 250                 255
Gln Gly Ala Gly Ala Ala Ala Ala Gly Gly Ala Gly Gln Gly Gly
            260                 265                 270
Tyr Gly Gly Leu Gly Ser Gln Gly Thr Ser Gly Arg Gly Gly Leu Gly
        275                 280                 285
Gly Gln Gly Ala Gly Ala Ala Ala Ala Gly Gly Ala Gly Gln Gly
            290                 295                 300
Gly Tyr Gly Gly Leu Gly Ser Gln Gly Thr Ser Gly Arg Gly Gly Leu
305                 310                 315                 320
Gly Gly Gln Gly Ala Gly Ala Ala Ala Ala Gly Gly Ala Gly Gln
            325                 330                 335
Gly Gly Tyr Gly Gly Leu Gly Ser Gln Gly Thr Ser Gly Arg Gly Gly
            340                 345                 350
Leu Gly Gly Gln Gly Ala Gly Ala Ala Ala Ala Gly Gly Ala Gly
            355                 360                 365
Gln Gly Gly Tyr Gly Gly Leu Gly Ser Gln Gly Thr Ser Gly Arg Gly
            370                 375                 380
Gly Leu Gly Gly Gln Gly Ala Gly Ala Ala Ala Ala Gly Gly Ala
385                 390                 395                 400
Gly Gln Gly Gly Tyr Gly Gly Leu Gly Ser Gln Gly Thr Ser Gly Arg
            405                 410                 415
Gly Gly Leu Gly Gly Gln Gly Ala Gly Ala Ala Ala Ala Gly Gly
            420                 425                 430
Ala Gly Gln Gly Gly Tyr Gly Gly Leu Gly Ser Gln Gly Thr Ser Gly
            435                 440                 445
Arg Gly Gly Leu Gly Gly Gln Gly Ala Gly Ala Ala Ala Ala Gly
450                 455                 460
Gly Ala Gly Gln Gly Gly Tyr Gly Gly Leu Gly Ser Gln Gly Thr Ser
465                 470                 475                 480
Gly Arg Gly Gly Leu Gly Gly Gln Gly Ala Gly Ala Ala Ala Ala
            485                 490                 495
Gly Gly Ala Gly Gln Gly Gly Tyr Gly Gly Leu Gly Ser Gln Gly Thr
            500                 505                 510
Ser Arg Gly Asp Cys Gly Ser Leu Pro Val Ala Arg Tyr Gln Asn Thr
            515                 520                 525
Glu Ser Glu Ser Glu Glu Arg Thr Gly Asn Leu Ala Gln Ser Pro
            530                 535                 540
Pro Pro Pro Met Ala Asn Ser Asp His Thr Asp Ser Ser Glu Ser Gly
545                 550                 555                 560
Glu Glu Leu Gly Ser Asp Arg Ser Gln Tyr Arg Pro Ala Gly Leu
            565                 570                 575
Ser Lys Ser Ala Gly Met Asp Ala Asp Lys Glu Glu Asp Glu Asp
            580                 585                 590
Ser Gly Asp Asp Thr Phe Gly Asp Glu Asp Asn Gly Pro Gly Pro Glu
            595                 600                 605
Glu Arg Gln Trp Gly Gly Pro Ser Arg Leu Asp Ser Asp Glu Asp Ser
            610                 615                 620
Ala Asp Thr Thr Gln Ser Ser Glu Asp Ser Thr Ser Gln Glu Asn Ser
625                 630                 635                 640
```

```
Ala Gln Asp Thr Pro Ser Asp Ser Lys Asp His His Ser Asp Glu Ala
                645                 650                 655

Asp Ser Arg Pro Glu Ala Gly Asp Ser Thr Gln Asp Ser Glu Ser Glu
            660                 665                 670

Glu Tyr Arg Val Gly Gly Gly Ser Gly Glu Ser Ser His Gly Asp
                675                 680                 685

Gly Ser Glu Phe Asp Asp Glu Gly Met Gln Ser Asp Pro Gly Ser
        690                 695                 700

Thr Arg Ser Asp Arg Gly His Thr Arg Met Ser Ser Ala Asp Ile Ser
705                 710                 715                 720

Ser Glu Glu Ser Lys Gly Asp His Glu Pro Thr Ser Thr Gln Asp Ser
                725                 730                 735

Asp Asp Ser Gln Asp Val Glu Phe Ser Ser Arg Lys Ser Phe Arg Arg
            740                 745                 750

Ser Arg Val Ser Glu Glu Asp Arg Gly Glu Leu Ala Asp Ser Asn
        755                 760                 765

Ser Arg Glu Thr Gln Ser Val Ser Thr Glu Asp Phe Arg Ser Lys Glu
        770                 775                 780

Glu Ser Arg Ser Glu Thr Gln Glu Asp Thr Ala Glu Thr Gln Ser Gln
785                 790                 795                 800

Glu Asp Ser Pro Glu Gly Gln Asp Pro Ser Glu Ser Ser Glu Glu
                805                 810                 815

Ala Gly Glu Pro Ser Gln Glu Ser Ser Glu Ser Gln Glu Gly Val
                820                 825                 830

Ala Ser Glu Ser Arg Gly Asp Asn Pro Asp Asn Thr Ser Gln Thr Gly
        835                 840                 845

Asp Gln Arg Asp Ser Glu Ser Ser Glu Glu Asp Arg Leu Asn Thr Phe
        850                 855                 860

Ser Ser Ser Glu Ser Gln Ser Thr Glu Glu Gln Gly Asp Ser Glu Ser
865                 870                 875                 880

Asn Glu Ser Leu Ser Leu Ser Glu Glu Ser Gln Glu Ser Ala Gln Asp
                885                 890                 895

Glu Asp Ser Ser Ser Gln Glu Gly Leu Gln Ser Gln Ser Ala Ser Arg
            900                 905                 910

Glu Ser Arg Ser Gln Glu Ser Gln Ser Glu Glu Asp Ser Arg Ser Glu
            915                 920                 925

Glu Asn Arg Asp Ser Asp Ser Gln Asp Ser Ser Arg Ser Lys Glu Glu
        930                 935                 940

Ser Asn Ser Thr Gly Ser Thr Ser Ser Ser Glu Glu Asp Asn His Pro
945                 950                 955                 960

Lys Asn Ile Glu Ala Asp Asn Arg Lys Leu Ile Val Asp Ala Tyr His
                965                 970                 975

Asn Lys Pro Ile Gly Asp Gln Asp Asp Asn Asp Cys Gln Asp Gly Tyr
            980                 985                 990

<210> SEQ ID NO 11
<211> LENGTH: 568
<212> TYPE: PRT
<213> ORGANISM: Artificial Sequence
<220> FEATURE:
<223> OTHER INFORMATION: Description of Artificial Sequence: Synthetic
      fusion protein

<400> SEQUENCE: 11

Met Ala Ser Met Thr Gly Gly Gln Gln Met Gly Arg Gly Ser Ala Met
1               5                   10                  15
```

```
Ala Ser Gly Arg Gly Gly Leu Gly Gly Gln Gly Ala Gly Ala Ala Ala
            20                  25                  30
Ala Ala Gly Gly Ala Gly Gln Gly Gly Tyr Gly Gly Leu Gly Ser Gln
            35                  40                  45
Gly Thr Ser Gly Arg Gly Gly Leu Gly Gly Gln Gly Ala Gly Ala Ala
        50                  55                  60
Ala Ala Ala Gly Gly Ala Gly Gln Gly Gly Tyr Gly Gly Leu Gly Ser
65                  70                  75                  80
Gln Gly Thr Ser Gly Arg Gly Gly Leu Gly Gly Gln Gly Ala Gly Ala
                85                  90                  95
Ala Ala Ala Ala Gly Gly Ala Gly Gln Gly Gly Tyr Gly Gly Leu Gly
                100                 105                 110
Ser Gln Gly Thr Ser Gly Arg Gly Gly Leu Gly Gly Gln Gly Ala Gly
                115                 120                 125
Ala Ala Ala Ala Ala Gly Gly Ala Gly Gln Gly Gly Tyr Gly Gly Leu
            130                 135                 140
Gly Ser Gln Gly Thr Ser Gly Arg Gly Gly Leu Gly Gly Gln Gly Ala
145                 150                 155                 160
Gly Ala Ala Ala Ala Gly Gly Ala Gly Gln Gly Gly Tyr Gly Gly
                165                 170                 175
Leu Gly Ser Gln Gly Thr Ser Gly Arg Gly Gly Leu Gly Gly Gln Gly
            180                 185                 190
Ala Gly Ala Ala Ala Ala Gly Gly Ala Gly Gln Gly Gly Tyr Gly
            195                 200                 205
Gly Leu Gly Ser Gln Gly Thr Ser Gly Arg Gly Gly Leu Gly Gly Gln
        210                 215                 220
Gly Ala Gly Ala Ala Ala Ala Gly Gly Ala Gly Gln Gly Gly Tyr
225                 230                 235                 240
Gly Gly Leu Gly Ser Gln Gly Thr Ser Gly Arg Gly Gly Leu Gly Gly
                245                 250                 255
Gln Gly Ala Gly Ala Ala Ala Ala Gly Gly Ala Gly Gln Gly Gly
                260                 265                 270
Tyr Gly Gly Leu Gly Ser Gln Gly Thr Ser Gly Arg Gly Gly Leu Gly
            275                 280                 285
Gly Gln Gly Ala Gly Ala Ala Ala Ala Gly Gly Ala Gly Gln Gly
            290                 295                 300
Gly Tyr Gly Gly Leu Gly Ser Gln Gly Thr Ser Gly Arg Gly Gly Leu
305                 310                 315                 320
Gly Gly Gln Gly Ala Gly Ala Ala Ala Ala Gly Gly Ala Gly Gln
                325                 330                 335
Gly Gly Tyr Gly Gly Leu Gly Ser Gln Gly Thr Ser Gly Arg Gly Gly
                340                 345                 350
Leu Gly Gly Gln Gly Ala Gly Ala Ala Ala Ala Gly Gly Ala Gly
            355                 360                 365
Gln Gly Gly Tyr Gly Gly Leu Gly Ser Gln Gly Thr Ser Gly Arg Gly
            370                 375                 380
Gly Leu Gly Gly Gln Gly Ala Gly Ala Ala Ala Ala Gly Gly Ala
385                 390                 395                 400
Gly Gln Gly Gly Tyr Gly Gly Leu Gly Ser Gln Gly Thr Ser Gly Arg
                405                 410                 415
Gly Gly Leu Gly Gly Gln Gly Ala Gly Ala Ala Ala Ala Gly Gly
                420                 425                 430
Ala Gly Gln Gly Gly Tyr Gly Gly Leu Gly Ser Gln Gly Thr Ser Gly
```

```
                    435                 440                 445
Arg Gly Gly Leu Gly Gly Gln Gly Ala Gly Ala Ala Ala Ala Gly
        450                 455                 460

Gly Ala Gly Gln Gly Gly Tyr Gly Gly Leu Gly Ser Gln Gly Thr Ser
465                 470                 475                 480

Gly Arg Gly Gly Leu Gly Gly Gln Gly Ala Gly Ala Ala Ala Ala
            485                 490                 495

Gly Gly Ala Gly Gln Gly Gly Tyr Gly Gly Leu Gly Ser Gln Gly Thr
                500                 505                 510

Ser Glu Phe Pro Val Gln Ser Ser Asp Ser Ser Glu Glu Asn Gly
            515                 520                 525

Asn Gly Asp Ser Ser Glu Glu Glu Glu Glu Glu Glu Asn Ser Asn
        530                 535                 540

Glu Glu Glu Asn Asn Glu Glu Asn Glu Asp Ser Asp Gly Asn Glu Asp
545                 550                 555                 560

Lys Leu His His His His His His
                565

<210> SEQ ID NO 12
<211> LENGTH: 578
<212> TYPE: PRT
<213> ORGANISM: Artificial Sequence
<220> FEATURE:
<223> OTHER INFORMATION: Description of Artificial Sequence: Synthetic
      fusion protein

<400> SEQUENCE: 12

Met Ala Ser Met Thr Gly Gly Gln Gln Met Gly Arg Gly Ser Cys Arg
1               5                   10                  15

Gly Asp Thr Ser Gly Arg Gly Gly Leu Gly Gly Gln Gly Ala Gly Ala
            20                  25                  30

Ala Ala Ala Gly Gly Ala Gly Gln Gly Gly Tyr Gly Gly Leu Gly
        35                  40                  45

Ser Gln Gly Thr Ser Gly Arg Gly Gly Leu Gly Gly Gln Gly Ala Gly
    50                  55                  60

Ala Ala Ala Ala Gly Gly Ala Gly Gln Gly Gly Tyr Gly Gly Leu
65                  70                  75                  80

Gly Ser Gln Gly Thr Ser Gly Arg Gly Gly Leu Gly Gly Gln Gly Ala
                85                  90                  95

Gly Ala Ala Ala Ala Gly Gly Ala Gly Gln Gly Gly Tyr Gly Gly
            100                 105                 110

Leu Gly Ser Gln Gly Thr Ser Gly Arg Gly Gly Leu Gly Gly Gln Gly
        115                 120                 125

Ala Gly Ala Ala Ala Ala Gly Gly Ala Gly Gln Gly Gly Tyr Gly
    130                 135                 140

Gly Leu Gly Ser Gln Gly Thr Ser Gly Arg Gly Gly Leu Gly Gly Gln
145                 150                 155                 160

Gly Ala Gly Ala Ala Ala Ala Gly Gly Ala Gly Gln Gly Gly Tyr
                165                 170                 175

Gly Gly Leu Gly Ser Gln Gly Thr Ser Gly Arg Gly Gly Leu Gly
            180                 185                 190

Gln Gly Ala Gly Ala Ala Ala Ala Gly Gly Ala Gly Gln Gly Gly
        195                 200                 205

Tyr Gly Gly Leu Gly Ser Gln Gly Thr Ser Gly Arg Gly Gly Leu Gly
    210                 215                 220

Gly Gln Gly Ala Gly Ala Ala Ala Ala Gly Gly Ala Gly Gln Gly
```

```
            225                 230                 235                 240
Gly Tyr Gly Gly Leu Gly Ser Gln Gly Thr Ser Gly Arg Gly Gly Leu
                245                 250                 255

Gly Gly Gln Gly Ala Gly Ala Ala Ala Ala Gly Gly Ala Gly Gln
        260                 265                 270

Gly Gly Tyr Gly Gly Leu Gly Ser Gln Gly Thr Ser Gly Arg Gly
        275                 280                 285

Leu Gly Gly Gln Gly Ala Gly Ala Ala Ala Ala Gly Gly Ala Gly
        290                 295                 300

Gln Gly Gly Tyr Gly Gly Leu Gly Ser Gln Gly Thr Ser Gly Arg Gly
305                 310                 315                 320

Gly Leu Gly Gly Gln Gly Ala Gly Ala Ala Ala Ala Gly Gly Ala
                325                 330                 335

Gly Gln Gly Gly Tyr Gly Gly Leu Gly Ser Gln Gly Thr Ser Gly Arg
                340                 345                 350

Gly Gly Leu Gly Gly Gln Gly Ala Gly Ala Ala Ala Ala Gly Gly
                355                 360                 365

Ala Gly Gln Gly Gly Tyr Gly Gly Leu Gly Ser Gln Gly Thr Ser Gly
        370                 375                 380

Arg Gly Gly Leu Gly Gly Gln Gly Ala Gly Ala Ala Ala Ala Gly
385                 390                 395                 400

Gly Ala Gly Gln Gly Gly Tyr Gly Gly Leu Gly Ser Gln Gly Thr Ser
                405                 410                 415

Gly Arg Gly Gly Leu Gly Gly Gln Gly Ala Gly Ala Ala Ala Ala
                420                 425                 430

Gly Gly Ala Gly Gln Gly Gly Tyr Gly Gly Leu Gly Ser Gln Gly Thr
        435                 440                 445

Ser Gly Arg Gly Gly Leu Gly Gly Gln Gly Ala Gly Ala Ala Ala
        450                 455                 460

Ala Gly Gly Ala Gly Gln Gly Gly Tyr Gly Gly Leu Gly Ser Gln Gly
465                 470                 475                 480

Thr Ser Gly Arg Gly Gly Leu Gly Gly Gln Gly Ala Gly Ala Ala
                485                 490                 495

Ala Ala Gly Gly Ala Gly Gln Gly Gly Tyr Gly Gly Leu Gly Ser Gln
        500                 505                 510

Gly Thr Ser Arg Gly Asp Cys Gly Ser Glu Ser Glu Phe Pro Val Gln
        515                 520                 525

Ser Ser Ser Asp Ser Ser Glu Glu Asn Gly Asn Gly Asp Ser Ser Glu
        530                 535                 540

Glu Glu Glu Glu Glu Glu Glu Asn Ser Asn Glu Glu Asn Asn Glu
545                 550                 555                 560

Glu Asn Glu Asp Ser Asp Gly Asn Glu Asp Lys Leu His His His His
                565                 570                 575

His His

<210> SEQ ID NO 13
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
ggatcctgtc gcggtgacac tagtcgcggt gactgtg                             37
```

```
<210> SEQ ID NO 14
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
ggatccacag tcaccgcgac tagtgtcacc gcgacag                              37

<210> SEQ ID NO 15
<211> LENGTH: 64
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
aattcagcag caaaaaaagc ggcagctatt cgggcagcaa aggcagcaaa cgccgcatcc     60
tcgc                                                                 64

<210> SEQ ID NO 16
<211> LENGTH: 64
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
gtcgtcgttt ttttcgccgt cgataagccc gtcgtttccg tcgtttgcgg cgtaggagcg    60
ccgg                                                                 64

<210> SEQ ID NO 17
<211> LENGTH: 19
<212> TYPE: PRT
<213> ORGANISM: Cylindrotheca fusiformis

<400> SEQUENCE: 17

Ser Ser Lys Lys Ser Gly Ser Tyr Ser Gly Ser Lys Gly Ser Lys
1               5                   10                  15

Arg Ile Leu

<210> SEQ ID NO 18
<211> LENGTH: 22
<212> TYPE: PRT
<213> ORGANISM: Cylindrotheca fusiformis

<400> SEQUENCE: 18

Ser Ser Lys Lys Ser Gly Ser Tyr Ser Gly Tyr Ser Thr Lys Lys Ser
1               5                   10                  15

Gly Ser Arg Arg Ile Leu
            20

<210> SEQ ID NO 19
<211> LENGTH: 20
<212> TYPE: PRT
<213> ORGANISM: Cylindrotheca fusiformis

<400> SEQUENCE: 19

Ser Ser Lys Lys Ser Gly Ser Tyr Ser Gly Tyr Ser Lys Gly Ser Lys
1               5                   10                  15
```

Arg Arg Ile Leu
        20

<210> SEQ ID NO 20
<211> LENGTH: 20
<212> TYPE: PRT
<213> ORGANISM: Cylindrotheca fusiformis

<400> SEQUENCE: 20

Ser Ser Lys Lys Ser Gly Ser Tyr Ser Gly Tyr Ser Lys Gly Ser Lys
1               5                   10                  15

Arg Arg Asn Leu
        20

<210> SEQ ID NO 21
<211> LENGTH: 15
<212> TYPE: PRT
<213> ORGANISM: Cylindrotheca fusiformis

<400> SEQUENCE: 21

Ser Ser Lys Lys Ser Gly Ser Tyr Tyr Ser Tyr Gly Thr Lys Lys
1               5                   10                  15

<210> SEQ ID NO 22
<211> LENGTH: 317
<212> TYPE: PRT
<213> ORGANISM: Homo sapiens

<400> SEQUENCE: 22

Met Lys Thr Ala Leu Ile Leu Leu Ser Ile Leu Gly Met Ala Cys Ala
1               5                   10                  15

Phe Ser Met Lys Asn Leu His Arg Arg Val Lys Ile Glu Asp Ser Glu
                20                  25                  30

Glu Asn Gly Val Phe Lys Tyr Arg Pro Arg Tyr Tyr Leu Tyr Lys His
            35                  40                  45

Ala Tyr Phe Tyr Pro His Leu Lys Arg Phe Pro Val Gln Gly Ser Ser
        50                  55                  60

Asp Ser Ser Glu Glu Asn Gly Asp Asp Ser Ser Glu Glu Glu Glu Glu
65                  70                  75                  80

Glu Glu Glu Thr Ser Asn Glu Gly Glu Asn Asn Glu Glu Ser Asn Glu
                85                  90                  95

Asp Glu Asp Ser Glu Ala Glu Asn Thr Thr Leu Ser Ala Thr Thr Leu
            100                 105                 110

Gly Tyr Gly Glu Asp Ala Thr Pro Gly Thr Gly Tyr Thr Gly Leu Ala
        115                 120                 125

Ala Ile Gln Leu Pro Lys Lys Ala Gly Asp Ile Thr Asn Lys Ala Thr
    130                 135                 140

Lys Glu Lys Glu Ser Asp Glu Glu Glu Glu Glu Glu Glu Glu Gly Asn
145                 150                 155                 160

Glu Asn Glu Glu Ser Glu Ala Glu Val Asp Glu Asn Glu Gln Gly Ile
                165                 170                 175

Asn Gly Thr Ser Thr Asn Ser Thr Glu Ala Glu Asn Gly Asn Gly Ser
            180                 185                 190

Ser Gly Gly Asp Asn Gly Glu Glu Gly Glu Glu Ser Val Thr Gly
        195                 200                 205

Ala Asn Ala Glu Gly Thr Thr Glu Thr Gly Gly Gln Gly Lys Gly Thr
    210                 215                 220

Ser Lys Thr Thr Thr Ser Pro Asn Gly Gly Phe Glu Pro Thr Thr Pro

```
                225                 230                 235                 240

Pro Gln Val Tyr Arg Thr Thr Ser Pro Pro Phe Gly Lys Thr Thr Thr
                245                 250                 255

Val Glu Tyr Glu Gly Glu Tyr Glu Tyr Thr Gly Val Asn Glu Tyr Asp
                260                 265                 270

Asn Gly Tyr Glu Ile Tyr Glu Ser Glu Asn Gly Glu Pro Arg Gly Asp
                275                 280                 285

Asn Tyr Arg Ala Tyr Glu Asp Glu Tyr Ser Tyr Phe Lys Gly Gln Gly
                290                 295                 300

Tyr Asp Gly Tyr Asp Gly Gln Asn Tyr Tyr His His Gln
305                 310                 315

<210> SEQ ID NO 23
<211> LENGTH: 265
<212> TYPE: PRT
<213> ORGANISM: Cylindrotheca fusiformis

<400> SEQUENCE: 23

Met Lys Leu Thr Ala Ile Phe Pro Leu Leu Phe Thr Ala Val Gly Tyr
1               5                   10                  15

Cys Ala Ala Gln Ser Ile Ala Asp Leu Ala Ala Ala Asn Leu Ser Thr
                20                  25                  30

Glu Asp Ser Lys Ser Ala Gln Leu Ile Ser Ala Asp Ser Ser Asp Asp
            35                  40                  45

Ala Ser Asp Ser Ser Val Glu Ser Val Asp Ala Ala Ser Ser Asp Val
        50                  55                  60

Ser Gly Ser Ser Val Glu Ser Val Asp Val Ser Gly Ser Ser Leu Glu
65                  70                  75                  80

Ser Val Asp Val Ser Gly Ser Leu Glu Ser Val Asp Asp Ser Ser
                85                  90                  95

Glu Asp Ser Glu Glu Glu Glu Leu Arg Ile Leu Ser Ser Lys Lys Ser
            100                 105                 110

Gly Ser Tyr Tyr Ser Tyr Gly Thr Lys Lys Ser Gly Ser Tyr Ser Gly
        115                 120                 125

Tyr Ser Thr Lys Lys Ser Ala Ser Arg Arg Ile Leu Ser Ser Lys Lys
    130                 135                 140

Ser Gly Ser Tyr Ser Gly Tyr Ser Thr Lys Lys Ser Gly Ser Arg Arg
145                 150                 155                 160

Ile Leu Ser Ser Lys Lys Ser Gly Ser Tyr Ser Gly Ser Lys Gly Ser
                165                 170                 175

Lys Arg Arg Ile Leu Ser Ser Lys Lys Ser Gly Ser Tyr Ser Gly Ser
            180                 185                 190

Lys Gly Ser Lys Arg Arg Asn Leu Ser Lys Lys Ser Gly Ser Tyr
        195                 200                 205

Ser Gly Ser Lys Gly Ser Lys Arg Arg Ile Leu Ser Ser Lys Lys Ser
    210                 215                 220

Gly Ser Tyr Ser Gly Ser Lys Gly Ser Lys Arg Arg Asn Leu Ser Ser
225                 230                 235                 240

Lys Lys Ser Gly Ser Tyr Ser Gly Ser Lys Gly Ser Lys Arg Arg Ile
                245                 250                 255

Leu Ser Gly Gly Leu Arg Gly Ser Met
            260                 265

<210> SEQ ID NO 24
<211> LENGTH: 551
<212> TYPE: PRT
```

<213> ORGANISM: Cylindrotheca fusiformis

<400> SEQUENCE: 24

| Met | Ala | Ser | Met | Thr | Gly | Gly | Gln | Gln | Met | Gly | Arg | Gly | Ser | Cys | Arg |
|---|---|---|---|---|---|---|---|---|---|---|---|---|---|---|---|
| 1 | | | | 5 | | | | | 10 | | | | | 15 | |

Gly Asp Thr Ser Gly Arg Gly Gly Leu Gly Gly Gln Gly Ala Gly Ala
                20                      25                      30

Ala Ala Ala Ala Gly Gly Ala Gly Gln Gly Gly Tyr Gly Gly Leu Gly
        35                      40                      45

Ser Gln Gly Thr Ser Gly Arg Gly Gly Leu Gly Gly Gln Gly Ala Gly
 50                         55                      60

Ala Ala Ala Ala Ala Gly Gly Ala Gly Gln Gly Gly Tyr Gly Gly Leu
65               70                      75                      80

Gly Ser Gln Gly Thr Ser Gly Arg Gly Gly Leu Gly Gly Gln Gly Ala
                85                      90                      95

Gly Ala Ala Ala Ala Gly Gly Ala Gly Gln Gly Gly Tyr Gly Gly
                100                    105                    110

Leu Gly Ser Gln Gly Thr Ser Gly Arg Gly Gly Leu Gly Gly Gln Gly
        115                      120                    125

Ala Gly Ala Ala Ala Ala Gly Gly Ala Gly Gln Gly Gly Tyr Gly
130                  135                    140

Gly Leu Gly Ser Gln Gly Thr Ser Gly Arg Gly Gly Leu Gly Gly Gln
145                 150                    155                    160

Gly Ala Gly Ala Ala Ala Ala Gly Gly Ala Gly Gln Gly Gly Tyr
                165                    170                    175

Gly Gly Leu Gly Ser Gln Gly Thr Ser Gly Arg Gly Gly Leu Gly
        180                      185                    190

Gln Gly Ala Gly Ala Ala Ala Ala Gly Gly Ala Gly Gln Gly Gly
                195                    200                    205

Tyr Gly Gly Leu Gly Ser Gln Gly Thr Ser Gly Arg Gly Gly Leu Gly
210                 215                    220

Gly Gln Gly Ala Gly Ala Ala Ala Ala Gly Gly Ala Gly Gln Gly
225                 230                    235                    240

Gly Tyr Gly Gly Leu Gly Ser Gln Gly Thr Ser Gly Arg Gly Gly Leu
        245                      250                    255

Gly Gly Gln Gly Ala Gly Ala Ala Ala Ala Gly Gly Ala Gly Gln
        260                      265                    270

Gly Gly Tyr Gly Gly Leu Gly Ser Gln Gly Thr Ser Gly Arg Gly Gly
            275                    280                    285

Leu Gly Gly Gln Gly Ala Gly Ala Ala Ala Ala Gly Gly Ala Gly
        290                      295                    300

Gln Gly Gly Tyr Gly Gly Leu Gly Ser Gln Gly Thr Ser Gly Arg Gly
305                 310                    315                    320

Gly Leu Gly Gly Gln Gly Ala Gly Ala Ala Ala Ala Gly Gly Ala
                325                    330                    335

Gly Gln Gly Gly Tyr Gly Gly Leu Gly Ser Gln Gly Thr Ser Gly Arg
        340                      345                    350

Gly Gly Leu Gly Gly Gln Gly Ala Gly Ala Ala Ala Ala Gly Gly
        355                      360                    365

Ala Gly Gln Gly Gly Tyr Gly Gly Leu Gly Ser Gln Gly Thr Ser Gly
        370                      375                    380

Arg Gly Gly Leu Gly Gly Gln Gly Ala Gly Ala Ala Ala Ala Gly
385                 390                    395                    400

Gly Ala Gly Gln Gly Gly Tyr Gly Gly Leu Gly Ser Gln Gly Thr Ser

```
                  405                 410                 415
Gly Arg Gly Gly Leu Gly Gly Gln Gly Ala Gly Ala Ala Ala Ala
            420                 425                 430

Gly Gly Ala Gly Gln Gly Gly Tyr Gly Gly Leu Gly Ser Gln Gly Thr
        435                 440                 445

Ser Gly Arg Gly Gly Leu Gly Gly Gln Gly Ala Gly Ala Ala Ala
        450                 455                 460

Ala Gly Gly Ala Gly Gln Gly Gly Tyr Gly Gly Leu Gly Ser Gln Gly
465                 470                 475                 480

Thr Ser Gly Arg Gly Gly Leu Gly Gly Gln Gly Ala Gly Ala Ala Ala
                485                 490                 495

Ala Ala Gly Gly Ala Gly Gln Gly Gly Tyr Gly Gly Leu Gly Ser Gln
            500                 505                 510

Gly Thr Ser Arg Gly Asp Cys Gly Ser Glu Phe Ser Lys Lys Ser
            515                 520                 525

Gly Ser Tyr Ser Gly Ser Lys Gly Ser Lys Arg Ile Leu Cys Gly
        530                 535                 540

Arg His His His His His His
545                 550

<210> SEQ ID NO 25
<211> LENGTH: 561
<212> TYPE: PRT
<213> ORGANISM: Cylindrotheca fusiformis

<400> SEQUENCE: 25

Met His His His His His Ser Ser Gly Leu Val Pro Arg Gly Ser
1               5                   10                  15

Gly Met Lys Glu Thr Ala Ala Ala Lys Phe Glu Arg Gln His Met Asp
            20                  25                  30

Ser Pro Asp Leu Gly Thr Asp Asp Asp Lys Ala Met Ala Ser Gly
        35                  40                  45

Arg Gly Gly Leu Gly Gly Gln Gly Ala Gly Ala Ala Ala Ala Gly
    50                  55                  60

Gly Ala Gly Gln Gly Gly Tyr Gly Gly Leu Gly Ser Gln Gly Thr Ser
65                  70                  75                  80

Gly Arg Gly Gly Leu Gly Gly Gln Gly Ala Gly Ala Ala Ala Ala
                85                  90                  95

Gly Gly Ala Gly Gln Gly Gly Tyr Gly Gly Leu Gly Ser Gln Gly Thr
            100                 105                 110

Ser Gly Arg Gly Gly Leu Gly Gly Gln Gly Ala Gly Ala Ala Ala
        115                 120                 125

Ala Gly Gly Ala Gly Gln Gly Gly Tyr Gly Gly Leu Gly Ser Gln Gly
    130                 135                 140

Thr Ser Gly Arg Gly Gly Leu Gly Gly Gln Gly Ala Gly Ala Ala Ala
145                 150                 155                 160

Ala Ala Gly Gly Ala Gly Gln Gly Gly Tyr Gly Gly Leu Gly Ser Gln
                165                 170                 175

Gly Thr Ser Gly Arg Gly Gly Leu Gly Gly Gln Gly Ala Gly Ala Ala
            180                 185                 190

Ala Ala Ala Gly Gly Ala Gly Gln Gly Gly Tyr Gly Gly Leu Gly Ser
        195                 200                 205

Gln Gly Thr Ser Gly Arg Gly Gly Leu Gly Gly Gln Gly Ala Gly Ala
    210                 215                 220

Ala Ala Ala Ala Gly Gly Ala Gly Gln Gly Gly Tyr Gly Gly Leu Gly
```

```
                225                 230                 235                 240
Ser Gln Gly Thr Ser Gly Arg Gly Gly Leu Gly Gly Gln Gly Ala Gly
                245                 250                 255

Ala Ala Ala Ala Ala Gly Gly Ala Gly Gln Gly Gly Tyr Gly Gly Leu
                260                 265                 270

Gly Ser Gln Gly Thr Ser Gly Arg Gly Gly Leu Gly Gly Gln Gly Ala
                275                 280                 285

Gly Ala Ala Ala Ala Ala Gly Gly Ala Gly Gln Gly Gly Tyr Gly Gly
                290                 295                 300

Leu Gly Ser Gln Gly Thr Ser Gly Arg Gly Gly Leu Gly Gly Gln Gly
305                 310                 315                 320

Ala Gly Ala Ala Ala Ala Ala Gly Gly Ala Gly Gln Gly Gly Tyr Gly
                325                 330                 335

Gly Leu Gly Ser Gln Gly Thr Ser Gly Arg Gly Gly Leu Gly Gly Gln
                340                 345                 350

Gly Ala Gly Ala Ala Ala Ala Ala Gly Gly Ala Gly Gln Gly Gly Tyr
                355                 360                 365

Gly Gly Leu Gly Ser Gln Gly Thr Ser Gly Arg Gly Gly Leu Gly Gly
                370                 375                 380

Gln Gly Ala Gly Ala Ala Ala Ala Ala Gly Gly Ala Gly Gln Gly Gly
385                 390                 395                 400

Tyr Gly Gly Leu Gly Ser Gln Gly Thr Ser Gly Arg Gly Gly Leu Gly
                405                 410                 415

Gly Gln Gly Ala Gly Ala Ala Ala Ala Ala Gly Gly Ala Gly Gln Gly
                420                 425                 430

Gly Tyr Gly Gly Leu Gly Ser Gln Gly Thr Ser Gly Arg Gly Gly Leu
                435                 440                 445

Gly Gly Gln Gly Ala Gly Ala Ala Ala Ala Ala Gly Gly Ala Gly Gln
                450                 455                 460

Gly Gly Tyr Gly Gly Leu Gly Ser Gln Gly Thr Ser Gly Arg Gly Gly
465                 470                 475                 480

Leu Gly Gly Gln Gly Ala Gly Ala Ala Ala Ala Ala Gly Gly Ala Gly
                485                 490                 495

Gln Gly Gly Tyr Gly Gly Leu Gly Ser Gln Gly Thr Ser Gly Arg Gly
                500                 505                 510

Gly Leu Gly Gly Gln Gly Ala Gly Ala Ala Ala Ala Ala Gly Gly Ala
                515                 520                 525

Gly Gln Gly Gly Tyr Gly Gly Leu Gly Ser Gln Gly Thr Ser Ser Ser
                530                 535                 540

Lys Lys Ser Gly Ser Tyr Ser Gly Ser Lys Gly Ser Lys Arg Arg Ile
545                 550                 555                 560

Leu

<210> SEQ ID NO 26
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
caggatccag gggtgacaac ccagat                                              26

<210> SEQ ID NO 27
<211> LENGTH: 26
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
gcctcgaggt agccatcttg gcaatc                                          26
```